US011155778B2

(12) United States Patent
Welch et al.

(10) Patent No.: US 11,155,778 B2
(45) Date of Patent: *Oct. 26, 2021

(54) CLOSED SYSTEM DEVICE AND METHODS FOR GAS PERMEABLE CELL CULTURE PROCESS

(71) Applicant: Wilson Wolf Manufacturing, New Brighton, MN (US)

(72) Inventors: Daniel P. Welch, Zimmerman, MN (US); John R. Wilson, New Brighton, MN (US)

(73) Assignee: Wilson Wolf Manufacturing, New Brighton, MN (US)

( * ) Notice: Subject to any disclaimer, the term of this patent is extended or adjusted under 35 U.S.C. 154(b) by 331 days.

This patent is subject to a terminal disclaimer.

(21) Appl. No.: 15/726,060

(22) Filed: Oct. 5, 2017

(65) Prior Publication Data

US 2018/0037864 A1 Feb. 8, 2018

Related U.S. Application Data

(63) Continuation of application No. 14/313,702, filed on Jun. 24, 2014, now Pat. No. 9,840,692.

(60) Provisional application No. 61/838,730, filed on Jun. 24, 2013.

(51) Int. Cl.
*C12M 1/00* (2006.01)
*C12Q 3/00* (2006.01)
*C12M 1/04* (2006.01)
*C12M 1/34* (2006.01)
*C12M 1/36* (2006.01)

(52) U.S. Cl.
CPC ............ *C12M 47/02* (2013.01); *C12M 23/24* (2013.01); *C12M 29/04* (2013.01); *C12M 41/34* (2013.01); *C12M 41/44* (2013.01); *C12M 41/48* (2013.01); *C12Q 3/00* (2013.01)

(58) Field of Classification Search
CPC ...... C12M 47/02; C12M 27/24; C12M 41/44; C12M 29/04; C12Q 3/00
See application file for complete search history.

(56) References Cited

U.S. PATENT DOCUMENTS

| | | | |
|---|---|---|---|
| 7,956,162 B2 | 6/2011 | Chahal et al. | |
| 7,956,164 B2 | 6/2011 | Har-Noy | |
| 8,146,446 B1 | 4/2012 | Wick | |
| 8,809,044 B2 | 8/2014 | Wilson | |
| 8,809,050 B2 | 8/2014 | Vera et al. | |
| 8,956,860 B2 | 2/2015 | Vera et al. | |
| 9,255,243 B2 | 2/2016 | Wilson et al. | |
| 9,315,774 B2* | 4/2016 | Knaus | C12M 37/02 |
| 2005/0032211 A1 | 2/2005 | Shaaltiel | |
| 2005/0054028 A1 | 3/2005 | Teich et al. | |
| 2007/0148764 A1 | 6/2007 | Suzuki et al. | |
| 2009/0130704 A1 | 5/2009 | Gyure | |
| 2010/0012260 A1 | 1/2010 | Brennan et al. | |
| 2010/0042260 A1 | 2/2010 | Antwiler | |
| 2011/0136228 A1* | 6/2011 | Vera | C12N 5/0636 435/373 |
| 2012/0077243 A1 | 3/2012 | Niazi | |
| 2012/0122201 A1 | 5/2012 | Butler et al. | |
| 2013/0102075 A1 | 4/2013 | Vera et al. | |
| 2013/0115617 A1 | 5/2013 | Wilson | |
| 2014/0377739 A1 | 12/2014 | Welch et al. | |

FOREIGN PATENT DOCUMENTS

| | | |
|---|---|---|
| CN | 201686685 | 12/2010 |
| CN | 102033012 | 4/2011 |
| JP | H08-172956 A | 7/1996 |
| JP | 2010-268813 | 12/2010 |
| WO | WO 2008/151093 | 12/2008 |
| WO | WO 2011/142667 | 11/2011 |

OTHER PUBLICATIONS

Search Report from Singapore Application No. 10201705494Y, dated Oct. 10, 2018, 2 pgs.
Examination Report from Singapore Application 11201510526V dated Apr. 27, 2017, 3 pgs.
Extended European Search Report for EP Application 14818630.7, dated Apr. 6, 2017, 3 pgs.
Written Opinion from Singapore Patent Application No. 1120150526V, dated Sep. 6, 2016, 3 pgs.
International Preliminary Report on Patentability from PCT Application PCT/US2014/043914, dated Jan. 7, 2016, 8 pgs.
International Search Report and Written Opinion from PCT Application PCT/US2014/043914, dated Jun. 24, 2014, 7 pgs.
Application and File History for U.S. Appl. No. 14/313,702, filed Jun. 24, 2014, inventors Welch et al.

* cited by examiner

*Primary Examiner* — Susan M Hanley
*Assistant Examiner* — Paul C Martin
(74) *Attorney, Agent, or Firm* — Patterson Thuente Pedersen, P.A.

(57) ABSTRACT

Novel methods and apparatus are disclosed for cell culture and cell recovery. The methods and apparatus simplify the process of cell separation from media, minimize potential damage to gas permeable devices during fluid handling, and allow closed system automated cell culture and cell recovery from gas permeable devices.

19 Claims, 18 Drawing Sheets

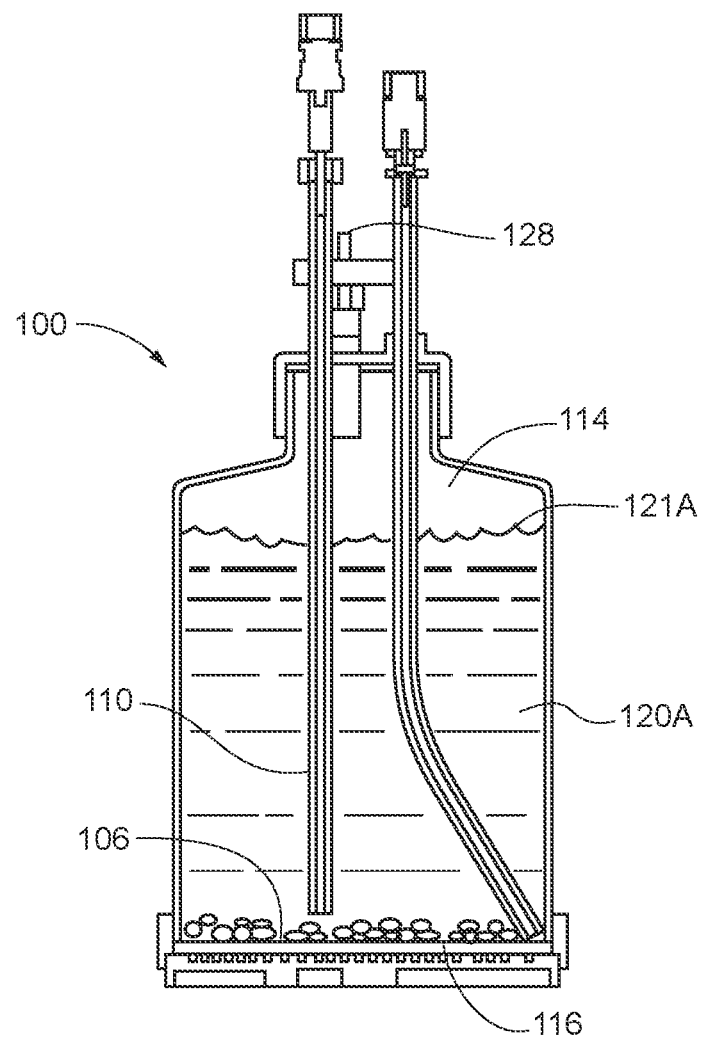
PRIOR ART

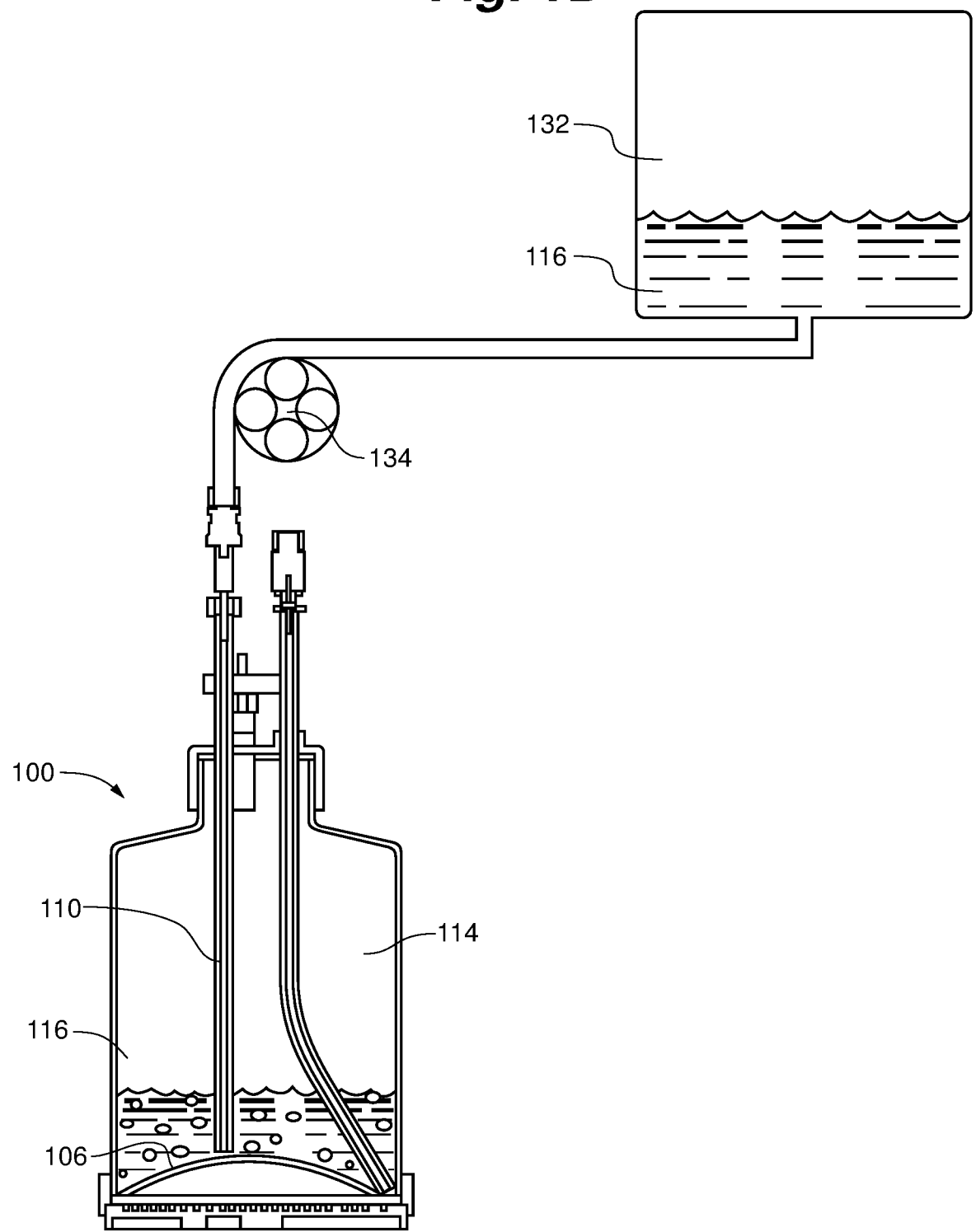

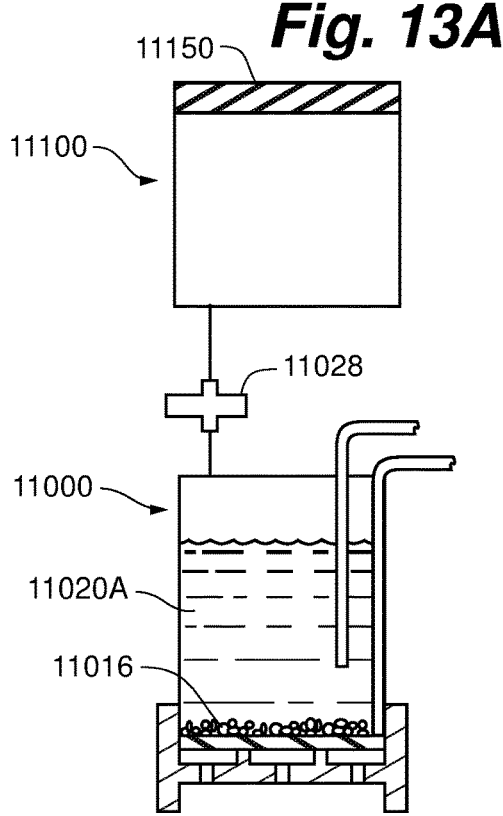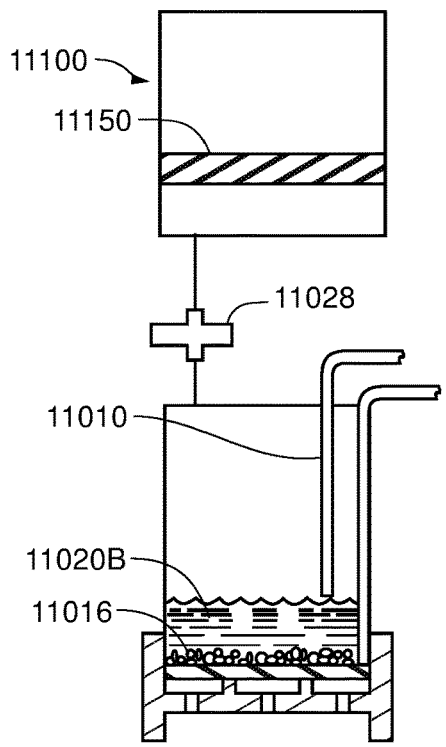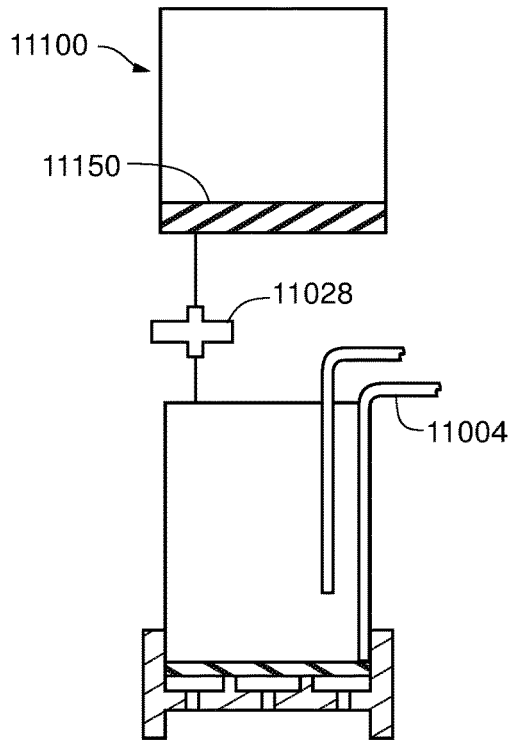

CLOSED SYSTEM DEVICE AND METHODS FOR GAS PERMEABLE CELL CULTURE PROCESS

RELATED APPLICATIONS

This application is a Continuation of U.S. patent application Ser. No. 14/313,702, filed Jun. 24, 2014 which claims the benefit of U.S. Provisional Patent Application No. 61/838,730, entitled "CLOSED SYSTEM DEVICE AND METHODS FOR GAS PERMEABLE CELL CULTURE PROCESS", and filed Jun. 24, 2013, said application being hereby fully incorporated herein by reference. Additionally, U.S. patent application Ser. No. 10/961,814 (hereinafter "814"), U.S. patent application Ser. No. 11/952,848 (hereinafter "848"), U.S. patent application Ser. No. 12/963,597 (hereinafter "597"), U.S. patent application Ser. No. 13/475,700 (hereinafter "700"), and U.S. patent application Ser. No. 13/493,768 (hereinafter "768") are incorporated herein by reference in their entirety.

TECHNICAL FIELD

The technical field of the invention relates to static cell culture methods and devices that efficiently expand cells within novel gas permeable cell culture devices and allow fluids to be added and removed from the culture system with little or no contamination risk, little or no loss of cells, and little or no distortion of gas permeable surfaces.

DISCUSSION OF LIMITATIONS OF CONVENTIONAL TECHNOLOGIES DESCRIBED IN RELATED ART

T cell therapy, adoptive immunotherapy, and adoptive cell therapy refer to powerful methods for treating various diseases that include expanding cells of the immune system in vitro and subsequently infusing the expanded cells into a patient to fight disease. For these forms of therapy to reach a wide segment of society, the process of expanding the a population of cells and collecting the cells needs to be cost effective, practical, not prone to cell loss, and have minimal to no contamination risk.

To date, there is not a cost effective and practical system for preparing and storing the cells produced in T cell therapy, adoptive immunotherapy, and adoptive cell therapy applications that is not subject to contamination and also does not require a significant amount of effort to separate cells from media after they have been produced. A key element of making the T cell production process practical for FDA approval is to minimize and even eliminate the chance for contamination, while minimizing process complexity. In the normal lexicon in this field, a culture process that is generally closed to contamination is commonly referred to as a "closed system." WAVE Bioreactor™, OriGen PermaLife™ bags, and/or VueLife® bags are the devices adapted for closed system T cell production. Bags have flexible housings that are able to collapse as media and cells are removed, typically by squeezing the bag, relying on gravity, and or by withdrawing media by peristaltic pumps. WAVE Bioreactor™ relies on peristaltic pumps to remove media and cells.

Recently G-Rex™ cell culture devices have become popular for T cell culture based on numerous advantages relative to WAVE Bioreactor™, OriGen PermaLife™ bags, and VueLife® bags. One of the advantages is described in '570 is the ability to remove the vast majority of media prior to collection of cells to minimize the amount of time and effort needed to separate cells from media. However, it has since been discovered that state-of-the-art methods of aforementioned methods do not work properly with G-Rex™ culture devices. G-Rex devices do not collapse as media is removed as do bags and use of peristaltic pumps to remove media from G-Rex devices puts the planar gas permeable surface in a state where it moves from its horizontal culture position and is pulled into the internal volume of the device by a vacuum that forms in the device. Attempts to prevent a vacuum from forming by use of larger and larger surface area vent filters have not led to a feasible configuration that allows the gas permeable surface to remain in a planar and/or horizontal position. Having the membrane pulled out of its planar and/or horizontal state is detrimental to the production process and creates the potential for cells to be lost when media volume is diminished or for leaks to form which can lead to contamination of the culture and/or expose workers to biohazards.

Thus, in order to simplify the process of cell recovery in a closed system manner, particularly for the field of T cell therapy, there exists a need to create a novel method of closed system fluid handling for gas permeable cell culture devices, including those disclosed in '814, '848, '597, '700, and '768.

SUMMARY OF THE INVENTION

Certain embodiments are disclosed that allow gas to displace a portion of an initial volume of media into a waste receptacle prior to displacing cells and a residual volume of media into a cell collection vessel.

One such embodiment discloses an apparatus for removing media from a cell culture device comprising a gas delivery component that is capable of connecting to a filter that is connected to a gas permeable cell culture device, said gas delivery component capable of delivering gas into said gas permeable cell culture device by way of said filter, a first fluid detection component that is capable of determining when the fluid moving within a media removal conduit that is connected to said gas permeable cell culture device changes from liquid to gas, said first fluid detection component capable of sending a signal to a first fluid flow control component that is capable of terminating fluid flow through said media removal conduit.

One such embodiment discloses an apparatus including a second fluid detection component that is capable of determining when fluid moving within a cell removal conduit that is connected to said gas permeable cell culture device changes from liquid to gas, said second fluid detection component capable of sending a signal to a second fluid flow control component capable of terminating fluid flow through said cell removal conduit.

One such embodiment discloses use of an apparatus for reducing the volume of liquid media in a gas permeable cell culture device that contains cells and media in order to increase the concentration of cells per milliliter of media by connecting a gas delivery component to a filter that is connected to the gas permeable cell culture device, a cell culture device including a media removal conduit, connecting a first fluid detection component to the media removal conduit, connecting a first fluid flow control component to the media removal conduit, initiating gas delivery from the gas delivery component, whereby gas moves into the cell culture device, the gas displaces media from the cell culture device into a media collection vessel connected to the media removal conduit, the first fluid detection component determines when the fluid that is moving through the media removal conduit has changed from liquid to gas and upon making that determination the first fluid detection component sends a signal to the first fluid flow control component, and upon the first fluid flow control component receiving the signal the first flow control component terminates the flow of fluid through the media removal conduit.

One such embodiment discloses use of an apparatus for collecting cells wherein after a first flow control component has terminated the flow of fluid through a media removal conduit, a cell collection vessel is connected to a media removal conduit, the media removal conduit having a media removal opening in contact with media, first flow control component opens the flow of fluid through the media removal conduit, gas delivered from the gas delivery component moves into the cell culture device, media and cells move through the media removal conduit into the cell collection vessel, the first fluid detection component determines when the fluid that is moving through the media removal conduit has changed from liquid to gas and sends a signal to the first fluid flow control component, and upon receiving the signal the first flow control component terminates the flow of fluid through the media removal conduit.

One such embodiment discloses increasing the number of cells per milliliter of media in a gas permeable cell culture device by connecting a gas delivery component to a filter that is connected to a gas permeable cell culture device containing liquid media and cells, at least a portion of the cells in contact with a growth surface within the cell culture device, the cell culture device including a media removal conduit and a cell removal conduit, connecting the first fluid detection component to the media removal conduit, connecting the first fluid flow control component to the media removal conduit, initiating gas delivery from the gas delivery component whereby gas moves into the cell culture device and the gas displaces media from the cell culture device into a media collection vessel connected to the media removal conduit, the first fluid detection component determining when the fluid that is moving through the media removal conduit has changed from liquid to gas and upon making that determination, the first fluid detection component sends a signal to the first fluid flow control component, and upon receiving said signal the first flow control component terminates the flow of fluid through the media removal conduit, and removing cells from the gas permeable cell culture device by connecting the second fluid detection component to the cell removal conduit, connecting the second fluid flow control component to the cell removal conduit, initiating gas delivery from the gas delivery component, whereby gas moves into the cell culture device and displaces media and cells by way of the cell removal conduit from the cell culture device into a cell collection vessel connected to the cell removal conduit, the second fluid detection component determining when the fluid that is moving through the cell removal conduit has changed from liquid to gas and when that is determined the second fluid detection component sends a signal to the second fluid flow control component and upon receiving said signal, the second flow control component terminates the flow of fluid through said cell removal conduit.

One such embodiment discloses collecting concentrated cells from a gas permeable cell culture device wherein after a second flow control component has terminated the flow of fluid through a cell removal conduit, the cell culture device is vented to atmosphere, first flow control component is opened to allow the flow of fluid through the media removal conduit, media is moved through the media removal conduit into the cell culture device, the first flow control component is closed, the media is agitated to move cells into the media, and the cell culture device is no longer vented to atmosphere and gas is delivered from the gas delivery component into the cell culture device and displaces media and cells from the cell culture device into a cell collection vessel connected to the cell removal conduit, the second fluid detection component determining when the fluid that is moving through the cell removal conduit has changed from liquid to gas and upon making that determination the second fluid detection component sends a signal to the second fluid flow control component and upon receiving the signal, the second flow control component terminates the flow of fluid through said cell removal conduit.

One such embodiment discloses increasing the number of cells per milliliter of media in a gas permeable cell culture device that contains a first volume of media and cells residing on a growth surface by reducing the volume of media in order to increase the concentration of cells per milliliter of media by connecting a gas delivery component to a filter that is connected to the cell culture device, the cell culture device including a media removal conduit, connecting a first fluid detection component to the media removal conduit, connecting a first fluid flow control component to a media removal conduit, initiating gas delivery from the gas delivery component, whereby gas moves into the cell culture device, the gas displaces media from the cell culture device into a media collection vessel connected to the media removal conduit, the first fluid detection component determines when the fluid that is moving through the media removal conduit has changed from media to gas and upon making that determination the first fluid detection component sends a signal to the first fluid flow control component, and upon said first fluid flow control component receiving the signal the first flow control component terminates the flow of fluid through the media removal conduit leaving a residual volume of media and cells within said cell culture device, the residual volume of media being less than the first volume of media.

One such embodiment discloses concentrating cells within a gas permeable cell culture device wherein after a first flow control component has terminated the flow of fluid through a media removal conduit, a cell collection vessel is connected to the media removal conduit, and with media in contact with a media removal opening of the media removal conduit first flow control component is opened to allow the flow of fluid through the media removal conduit, gas delivered from the gas delivery component moves into the cell culture device displacing the residual media volume and cells through the media removal conduit and into the cell collection vessel, the first fluid detection component determines when the fluid that is moving through the media removal conduit has changed from media to gas and sends a signal to the first fluid flow control component, and upon receiving the signal the first flow control component terminates the flow of fluid through said media removal conduit.

One such embodiment discloses collecting cells from a gas permeable cell culture device comprising a first step of reducing a first volume of media within a gas permeable cell culture device that contains cells in order to increase the concentration of cells per milliliter by connecting a gas delivery component to a filter that is connected to a gas permeable cell culture device containing media and cells, the cell culture device including a media removal conduit and a cell removal conduit, connecting a first fluid detection component to the media removal conduit, connecting a first fluid flow control component to the media removal conduit, and with at least a portion of the cells residing on a growth surface initiating gas delivery from the gas delivery component whereby gas moves into the cell culture device and the gas displaces media from the cell culture device into a media collection vessel connected to the media removal conduit, the first fluid detection component determining when the fluid that is moving through the media removal conduit has changed from media to gas and upon making that determination the first fluid detection component sends a signal to a first fluid flow control component, and upon receiving the signal the first flow control component terminates the flow of fluid through the media removal conduit leaving a residual volume of media and cells within the cell culture device, the residual volume of media being less than said first volume of media, and a second step of removing cells from the gas permeable cell culture device by connecting a second fluid detection component to the cell removal conduit, connecting a second fluid flow control component to the cell removal conduit, and with cells distributed throughout said residual volume of media initiating gas delivery from a gas delivery component, whereby gas moves into the cell culture device and displaces media and cells from the cell culture device into a cell collection vessel connected to said cell removal conduit, the second fluid detection component determining when the fluid that is moving through the cell removal conduit has changed from media to gas and when that determination is made the second fluid detection component sends a signal to the second fluid flow control component and upon receiving the signal, the second flow control component terminates the flow of fluid through the cell removal conduit.

One such embodiment discloses collecting cells including an additional step of rinsing the cell culture device to gather additional cells that may have been left in the cell culture device and/or the cell removal conduit after the second flow control component has terminated the flow of fluid through the cell removal conduit further comprising initiating the flow of liquid through the media removal conduit when the cell culture device is vented to atmosphere, the liquid moving through said media removal conduit into the cell culture device, agitating the liquid to move cells within the cell culture device into the liquid, and initiating gas delivery from the gas delivery component into the cell culture device, the gas displacing liquid and cells from the cell culture device into the cell collection vessel via the cell removal conduit, the second fluid detection component determining when the fluid that is moving through the cell removal conduit has changed from liquid to gas and when that determination is made the second fluid detection component sends a signal to the second fluid flow control component and upon receiving the signal, the second flow control component terminates the flow of fluid through the cell removal conduit.

BRIEF DESCRIPTION OF THE DRAWINGS

FIG. 1A shows a cross-sectional view of a gas permeable cell culture device.

FIG. 1D shows a cross-sectional view of a gas permeable cell culture device with a waste receptacle attached to it, a peristaltic pump moving media into the waste receptacle, a growth surface moving out of a horizontal position, and cells entering the waste receptacle.

FIG. 13A, FIG. 13B, and FIG. 13C show a cross-sectional view of a gas permeable cell culture device and a process by which the growth surface remains in a planar position during media and cell removal.

DETAILED DESCRIPTION OF THE INVENTION

Figure 1B:
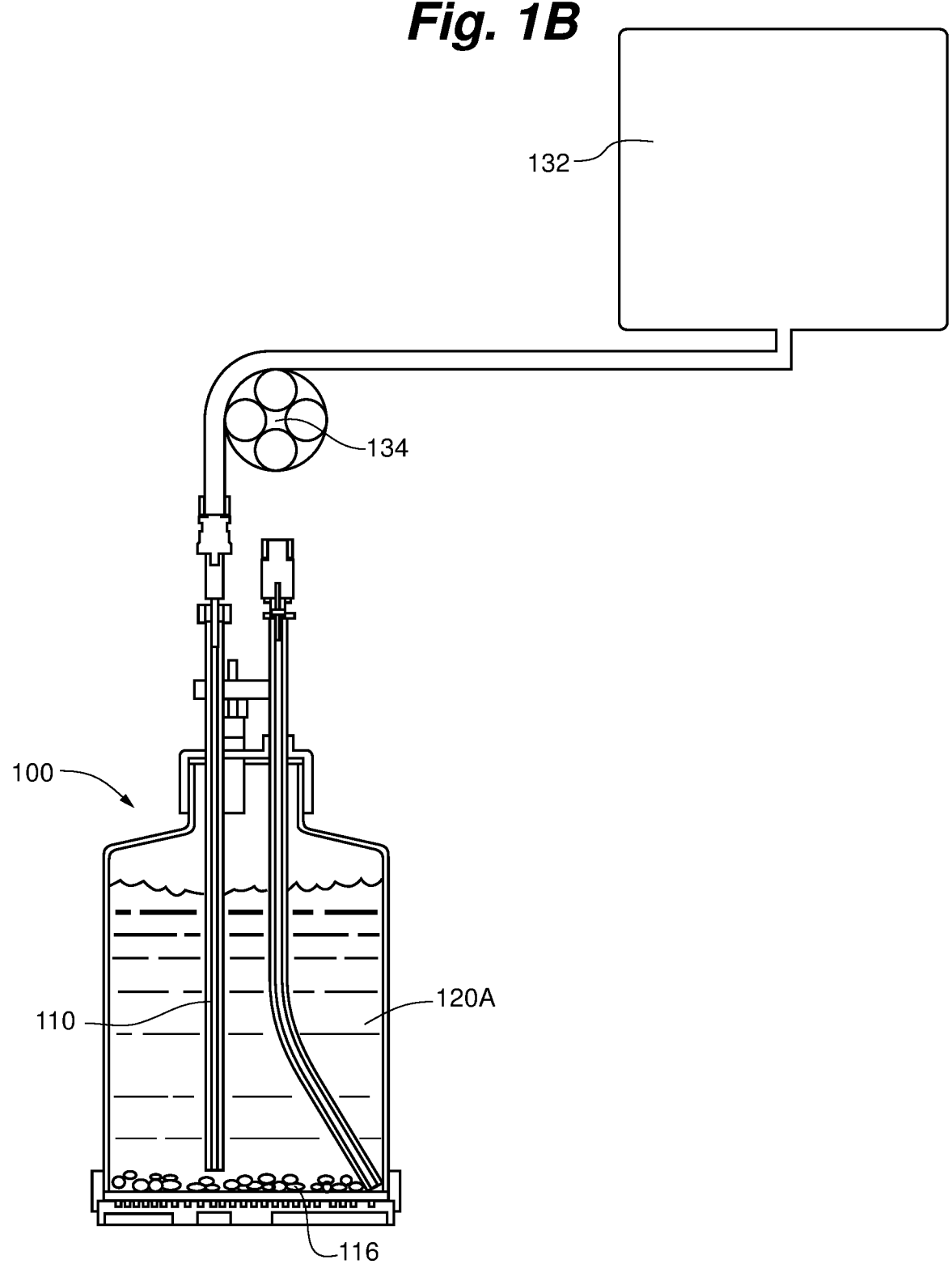
FIG. 1B shows a cross-sectional view of a gas permeable cell culture device with a waste receptacle attached to it.

Throughout this disclosure, unless otherwise specified, the following general considerations apply. Preferably when using the devices and methods disclosed herein, cells reside upon a gas permeable surface in a uniformly distributed state. Skilled artisans are advised to select gas permeable material that comports to that typically used in the cell culture field. Preferably, the gas permeable material is liquid impermeable. Additional guidance for the types of gas permeable surfaces that can be used is also found in co-pending '814, '848, '597, '700, and '768. When any type of non-adherent animal cells are the intended cells to be cultured, the gas permeable surface is preferably non-porous, liquid impermeable, and hydrophobic. Most preferably it is comprised of silicone and has a thickness between 0.001 inches and 0.024 inches. In the case of T cells in particular, silicone is a preferred material. Furthermore, the gas permeable material preferably resides in a horizontal position during culture in order for cells to gravitate to the gas permeable material and distribute across the entire surface of the gas permeable material, and more preferably in a uniform surface density. Skilled artisans are encouraged to recognize that through the present invention the word "horizontal" is inclusive of "substantially" horizontal, since under the weight of media the gas permeable material can move downward slightly in areas where it is not in direct contact with a support. The intent of a substantially horizontal orientation is to allow cells to distribute across the gas permeable material. Preferably the substantially horizontal state of the growth surface is such that it does not move out of plane by more than 20% of the surface area of the growth surface, more preferably 10%, even more preferably 5%, and most preferably 2.5%.

When the animal cells to be cultured include adherent cells, the gas permeable material is preferably hydrophilic and has an attachment friendly surface such as a plasma charged surface. Throughout this disclosure or any of the co-pending '814, '848, '597, '700, and '768 specifications, skilled artisans are advised to recognize that the term gas permeable membrane is synonymous with gas permeable material and is non limiting as skilled artisans are further advised to understand the word membrane is to be broadly defined as a gas permeable material of any of the forms of material known by those of ordinary skill in the art to be commonly used for cell culture devices and cell culture methods including those described in co-pending '814, '848, '597, '700, and '768. Throughout this disclosure the terms media and medium are synonymous with liquid that contains any variety of substrates and/or nutrients that are used for the culture of animal cells. Preferably, all materials of the device that can be exposed to fluid associated with the culture process are compatible with cell culture (e.g. USP VI, non-cytotoxic, meet acceptable leachable and particulate standards, etc.). Also, to ensure one can determine if cells are being lost during media removal, or assess the contents for any other reason, the cell culture and cell recovery device should preferably allow a visual assessment of the contents, as may be achieved by use of optically clear construction materials.

An aspect of one embodiment of the present invention can be found in co-pending '700 and its related drawing FIG. 22B, which is reproduced herein as FIG. 1A for illustrative purposes and for which item numbers have been altered from a 1000 series to a 100 series. In FIG. 1A, cell recovery device 100 is shown in operation at the point where the culture has been terminated and cells are about to be recovered. Cells 116 reside upon growth surface 106, which forms the bottom of the device and which is comprised of gas permeable material of the characteristics previously described. Initial media volume 120A resides at an initial media height 121A, which is equal to the distance from the highest media level to the lowest media level, that is preferably beyond the 1.0 cm height typical of static cell culture bags such as OriGen PermaLife™ and VueLife® bags. More preferably, initial media height 121A is at a height beyond 2.0 cm of medium. Although any height is possible, the optimal height will depend upon the specifics of the cell culture application. For example, as described in co-pending '700, when expanding CAR T cells without need of medium exchange, an initial media height of 10 cm is preferred if one seeks to allow a culture progress from a small number of cells to a much greater number of cells without need of medium exchange. Also, as media height increases, it makes it possible to remove a larger volume of media prior to collecting cells. We have discovered that cells submerged under an unconventionally high level of media do not easily become disbursed into the media as the media height is reduced. Skilled artisans should be aware that removing a large volume of media without disturbing cells can be very useful when seeking to perform media exchange (i.e. there is no requirement that cells be separated from the media that is removed in order to be reintroduced into the device and/or no requirement to split the culture to new devices) or when terminating the culture to recover cells (i.e. cell separation from the bulk of the media is performed in the device as opposed to use of cumbersome centrifugation equipment).

Figure 1C:
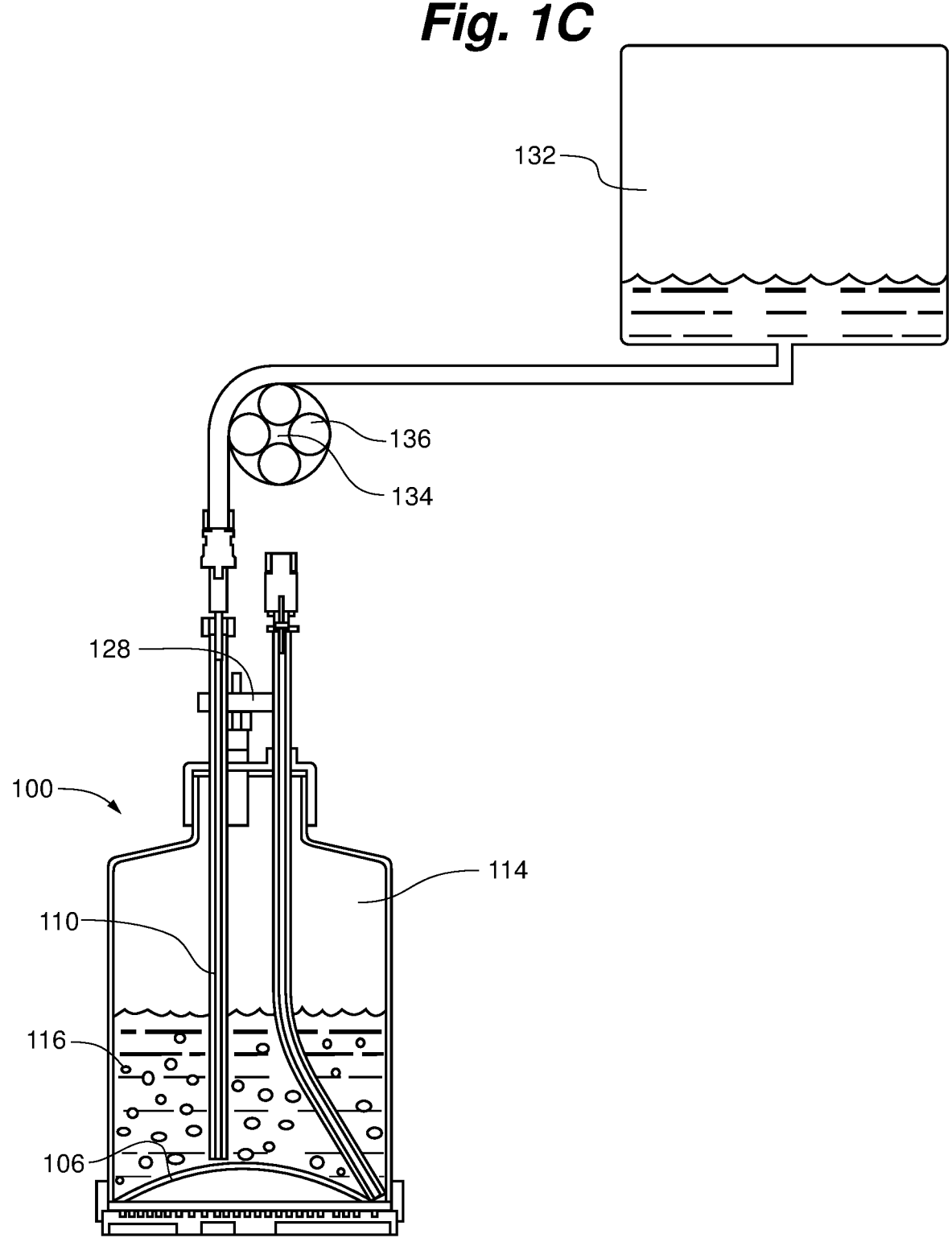
FIG. 1C shows a cross-sectional view of a gas permeable cell culture device with a waste receptacle attached to it, a peristaltic pump moving media into the waste receptacle, and a growth surface moving out of a horizontal position.

Unfortunately, it has been discovered that using standard closed system fluid handling methods to take full advantage of the novel capacity to reduce media volume in devices such as those disclosed in '814, '848, '597, '700, and '768 can lead to cell loss and damage the culture devices, which for T cell therapy, adoptive immunotherapy, and/or adoptive cell therapy applications can be catastrophic. Collectively, FIG. 1B, FIG. 1C, and FIG. 1D illustrate an example of the problems we have discovered in attempting to use traditional media handling tools and methods to reduce media volume prior to recovering cells from G-Rex™ devices and other gas permeable devices such as those disclosed in co-pending '814, '848, '597, '700, and '768. FIG. 1B shows the device described in FIG. 1A, after attaching waste receptacle 132 to media removal conduit 110. As a first step in reducing the amount of initial media volume 120A that cells 116 must be recovered from, a portion of initial media volume 120A is drawn from cell culture and cell recovery device 100 by pumping it into waste receptacle 132 via media removal conduit 110. A common method of pumping medium is by use of peristaltic pump 134 to draw media out of the culture device. As shown in FIG. 1C, as a portion of the initial media volume is removed from cell culture and cell recovery device 100, a pressure drop forms across sterile vent filter 128, placing internal volume 114 at a lower pressure relative to ambient atmosphere and typically a vacuum quickly forms within internal volume 114 of the device. Because growth surface 106 is preferably comprised of a gas permeable material with gas transfer characteristics that render it generally very thin and flimsy, when a vacuum forms growth surface 106 is drawn out of its preferred horizontal planar state very quickly to form a new, non-planar position as shown. Further, as rollers 136 of the peristaltic pump rotate, the gaps between the rollers cause the vacuum within the device to pulse, thereby pulsing distended growth surface 106, dislodging cells 116, and dispersing the dislodged cells throughout the medium. Subsequently, as shown in FIG. 1D, as media continues to be withdrawn into waste receptacle 132, cells 116 are also withdrawing in to waste receptacle 132. With this chain of events, the potential for a significant number of cells to be dispensed into the waste receptacle is great. Since patient outcomes are correlated to the number of cells in a treatment dose, loss of these precious cells is potentially catastrophic. Also, even if cells are not lost, the growth surface has the potential to be drawn to the media removal conduit making damage to the growth surface possible. For example a puncture of the growth surface can contaminate the culture rendering it unsuitable for patient use in addition to exposing those in the cell manufacturing facility to potential biohazards. Even if the growth surface is not damaged by the media removal conduit, if it is pulled into the media removal conduit it can be blocked, preventing any further removal of media and cells. In summary, drawing the growth surface out of its planar and preferably horizontal state can lead to cell loss, the inability to remove cells, damage to the growth surface due to its distension, damage to the growth surface due to physical contact with the media removal conduit, contamination of the culture, and/or exposure of production workers to biohazards. Thus, methods of cell recovery that avoid these pitfalls are needed.

In general, after performing cell culture and with cells having gravitated to the bottom of the device, which is comprised of gas permeable material, and when the device is still holding media, it is advantageous if a volume of gas is moved into the cell culture and cell recovery device in a manner that pressurizes the internal volume of the device. Preferably, a first volume of gas is moved into the device in order to move a first volume of media from the device into a waste receptacle. The step is preferable undertaken with the device oriented such that the growth surface upon which cells reside is oriented in a horizontal plane. When this step is complete, a residual volume of media remains within the device and cells also remain in the device. A second volume of as is then moved into the device, thereby displacing the residual volume of media and cells from the device and moving the residual volume of media and cells into a cell collection vessel. In the manner, the ratio of the volume of media to number of cells is reduced.

Figure 2A:
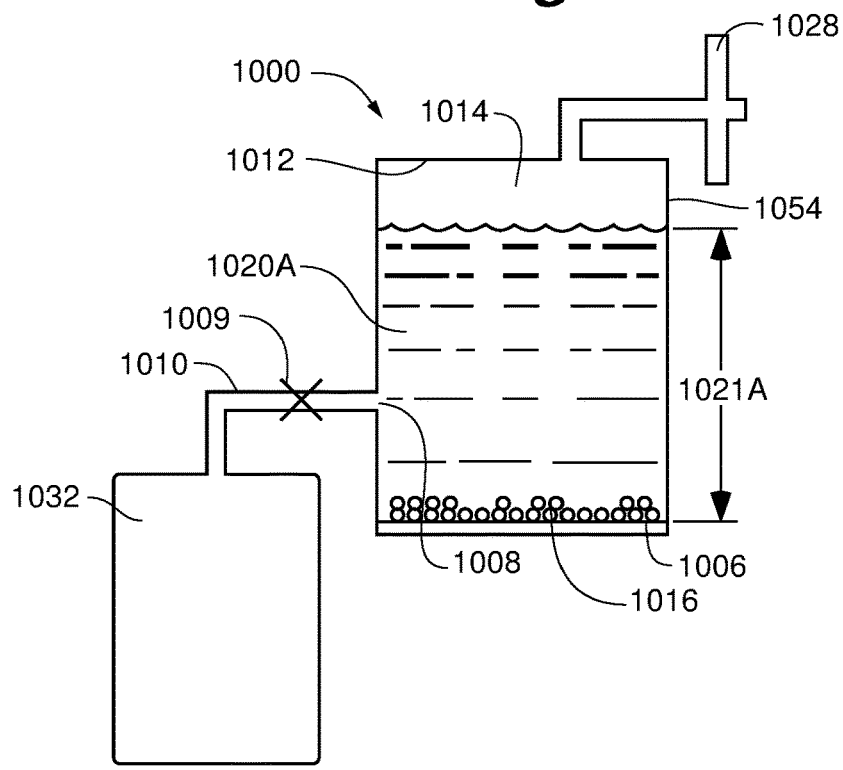
FIG. 2A shows a cross-sectional view of a gas permeable cell culture device with a waste receptacle attached to it.

FIG. 2A through FIG. 2E provide an illustrative example of an embodiment of the present invention that solves the problems shown in FIG. 1B through FIG. 1D by pushing gas into the cell culture and cell recovery device to drive media and/or media and cells from the device under pressure, as opposed to drawing media from the device under vacuum. This approach minimizes potential cell loss and/or damage to the device by preventing a vacuum from forming, preventing upward distortion of the growth surface, and/or preventing pulsing the growth surface in and out of a planar state which can quickly dislodge cells. In FIG. 2A, a cross-sectional view of cell culture and cell recovery device 1000 is shown in a cell culture position and in a state of static cell culture. Cell culture and cell recovery device 1000 comprises an internal volume 1014 bounded by an upper confine 1012 and a lower growth surface 1006, vent 1028, and media removal conduit 1010 with media removal opening 1008. Media removal conduit clamp 1009 is in the closed position to retain media within internal volume 1014. Preferably upper confine 1012 is adjoined to growth surface 1006 by sidewall(s) 1054 and more preferably sidewall(s) 1054 are perpendicular to growth surface 1006 and are rigid to allow cell inoculum to gravity uniformly onto growth surface 1006. An initial media volume 1020A is present in the device. Initial media volume 1020A resides within the confines of cell culture and cell recovery device 1000 at initial media height 1021A, which is equal to the distance from the uppermost media level to the lowermost media level. Cells 1016 are also present, which have gravitated upon growth surface 1006. Growth surface 1006 is preferably planar and oriented in a horizontal position during the culture process and is comprised of non-porous, gas permeable, liquid impermeable material, and is hydrophobic in the case where non-adherent cells are to be cultured. Media removal opening 1008 resides a distance from growth surface 1006 and as will be seen, the distance also constitutes a residual media height 1021B. At some point in the cell culture process, performing a media removal process that reduces initial media volume 1020A to a smaller residual media volume in order to either add fresh media or concentrate the cells in the residual media volume becomes desirable.

Figure 2B:
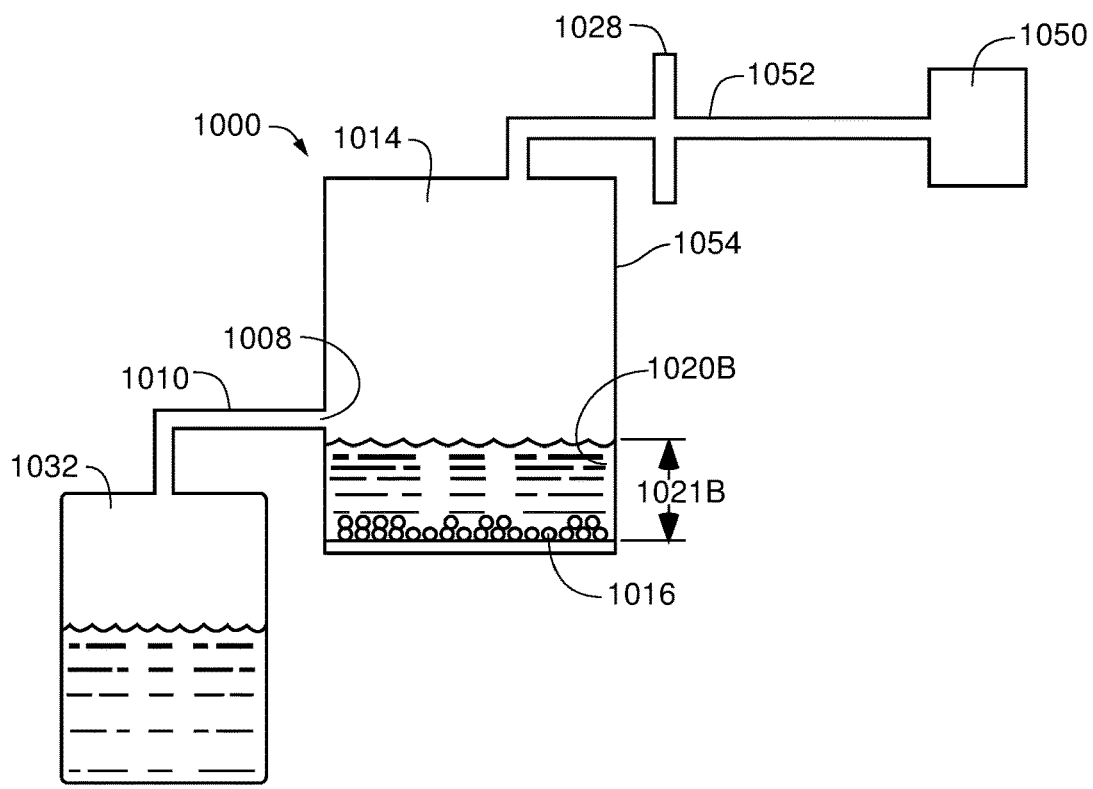
FIG. 2B shows a cross-sectional view of a gas permeable cell culture device with a waste receptacle attached to it, a peristaltic pump moving media into the waste receptacle, a growth surface remaining in a horizontal position, and an initial media volume having been reduced to a residual media volume in which cells reside.

To remove a portion of initial media volume 1020A, cell culture and cell recovery device 1000 is oriented in a position such that growth surface 1006 is at the bottom, and upper confine 1012 is at the top. Stated differently, cell culture and cell recovery device 1000 is oriented in its preferred static cell culture position. Cells 1016 reside on growth surface 1006 at an initial cell density, which is the quantity of cells 1016 divided by the initial media volume 1020A (e.g. cells/ml). Cells 1016 also reside on growth surface 1006 at an initial surface density, which is the quantity of cells 1016 divided by the surface area of growth surface 1006 upon which cells reside (e.g. cells/cm$^2$). A gas delivery component is connected to vent 1028, which is preferably located at the top of the device as best shown in FIG. 2B. Regardless, of however the internal volume of the cell culture and cell recovery device is vented, it is preferably by way of a gamma radiation stable material capable of sterile filtering gas, such as a 0.2 micron vent filter. In this example, the gas delivery component is diaphragm pump 1050 which is connected to vent 1028 by gas conduit 1052. When the gas delivery component is actively delivering gas (i.e. in this example when diaphragm pump 1050 is actuated), gas is driven into gas conduit 1052, through vent 1028, and into cell culture and cell recovery device 1000. Most preferably vent 1028 is comprised of a material capable of ensuring gas moving into cell culture and cell recovery device 1000 is sterile. Vent 1028 is also preferably oriented in a position that minimizes the opportunity for condensation to accumulate upon its filtration surface. In this depiction, the filtration surface of vent 1028 is not parallel to growth surface 1006 and is instead oriented perpendicular to growth surface 1006. As gas is delivered into cell culture and cell recovery device 1000 with media removal conduit clamp 1009 in the open position, a portion of initial media volume 1020A is displaced as it is driven into the media removal opening 1008, out of cell culture and cell recovery device 1000 by way of media removal conduit 1010, and into a waste receptacle, thereby leaving cells 1016 and a residual media volume 1020B, which resides at a residual media height 1021B. The waste receptacle need not be an enclosure and need not be physically attached to media removal conduit 1010. For example it could instead be something as common as a laboratory sink, but preferably the waste receptacle is an enclosed container such as a bag and is connected in a sealed manner to media removal conduit 1010 in order to isolate potential biohazards in a closed system manner. Such an enclosed container is represented in FIG. 2A and FIG. 2B as enclosed waste receptacle 1032 which is attached to media removal conduit 1010.

Preferably during this media removal process, growth surface 1006 is prevented from moving from its preferred horizontal position as gas enters cell culture and cell recovery device 1000 and the pressure of internal volume 1014 elevates. As will be described in the illustrative embodiments, this can be accomplished by a growth surface support, which holds the growth surface in a horizontal plane to prevent damage to the growth surface. Skilled artisans are advised to consult co-pending '814 and '848 for further guidance related to the growth surface support design.

Figure 2C:
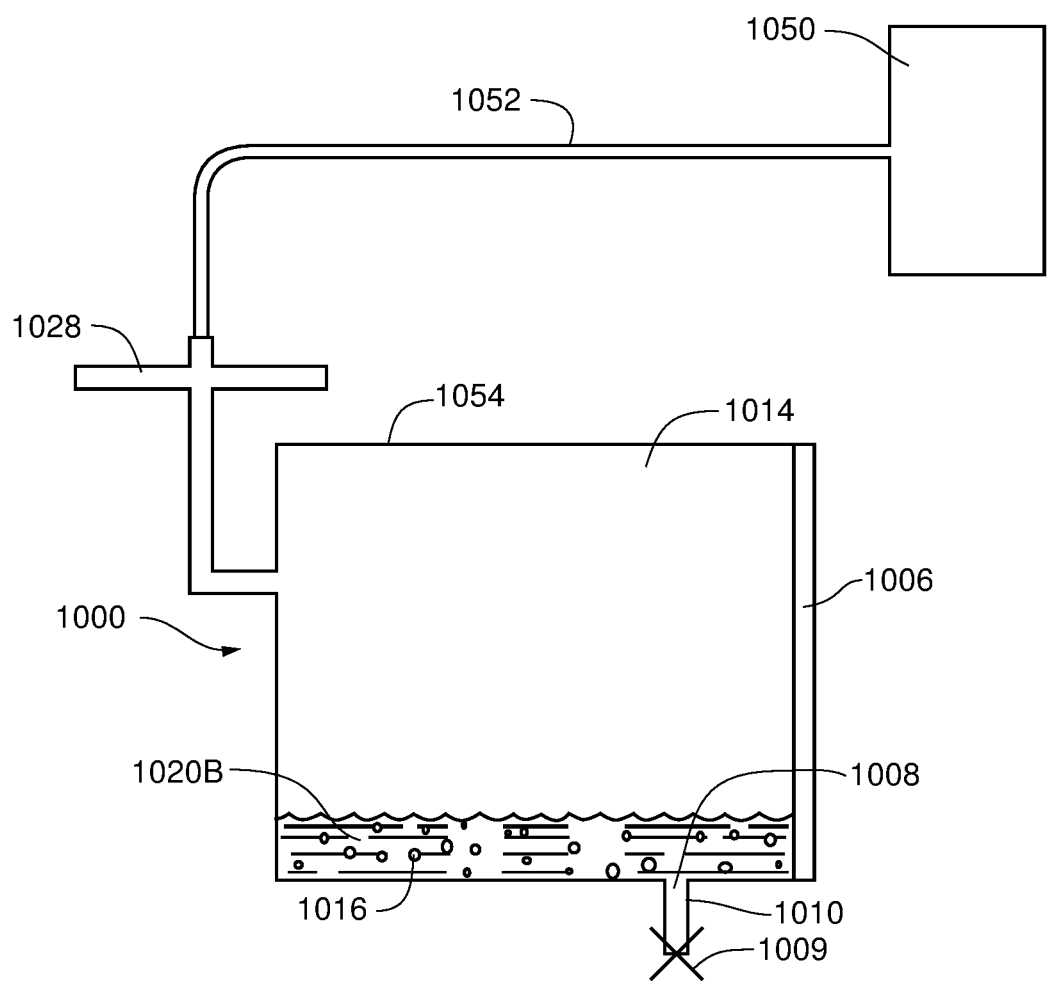
FIG. 2C shows a cross-sectional view of a gas permeable cell culture device after being oriented to a cell recovery position such that cells and residual media can be removed.

After the media removal process is complete, fresh media can be added by causing vent 1028 to be open to ambient atmosphere (e.g. disconnecting or venting gas conduit 1052) and adding fresh media via media removal conduit 1010 (or any other port that may present in the in the device and appropriately structured for that purpose). If there is no need of adding fresh media into the device and the culture is to be terminated, cells 1016 can be removed by reorienting cell culture and cell recovery device 1000 from its preferred static cell culture position, as shown in FIG. 2C, to a cell removal position in which media removal opening 1008 resides at a low point within internal volume 1014. Depending on the specific characteristics of the cells and the growth surface, it may be useful to agitate the residual media in the device to dislodge cells from the growth surface and suspend them into the residual media prior to attempting to remove cells from the device. We have discovered that non-adherent cells such as T cells, even when the growth surface is a hydrophobic gas permeable material such as silicone, have a tendency to remain piled upon the growth surface even when the device is tilted to the point where media no longer submerges the cells. Thus, to ensure cells are not left in the device when the residual media is removed, agitating the residual media to suspend cells within it prior to withdrawing residual media is preferred. Skilled artisans will recognize there are many ways of suspending cells in the residual media. For example, one may simply impart motion to the device to swirl the residual media about the device and over the growth surface and visually determine when the cells have dislodged from the growth surface and moved into the residual media. We have found that a cylindrical wall surrounding a circular growth surface facilitates this approach well. However this step is accomplished, once cells are dislodged from the growth surface and dispersed into the residual media, collection of cells can be undertaken by traditional methods of withdrawing the media and cells (such as by use of a peristaltic pump). However, withdrawing cells by drawing the media out of the device will cause the gas permeable material to move from a planar position as a vacuum forms in the device as a pressure drop across the vent occurs when the vent comprises a sterile filter. Yet, so long as the integrity of the gas permeable material is not breached as it moves from its horizontal position into a new position, or the integrity of any other aspect of the cell culture and cell recovery device is not affected, this can be done. However, a preferred method that does not put the gas permeable material or any other aspect of the cell culture and cell recovery device at risk of damage is to displace the residual media and cells by causing gas to be delivered into the cell culture and cell recovery device.

Figure 2D:
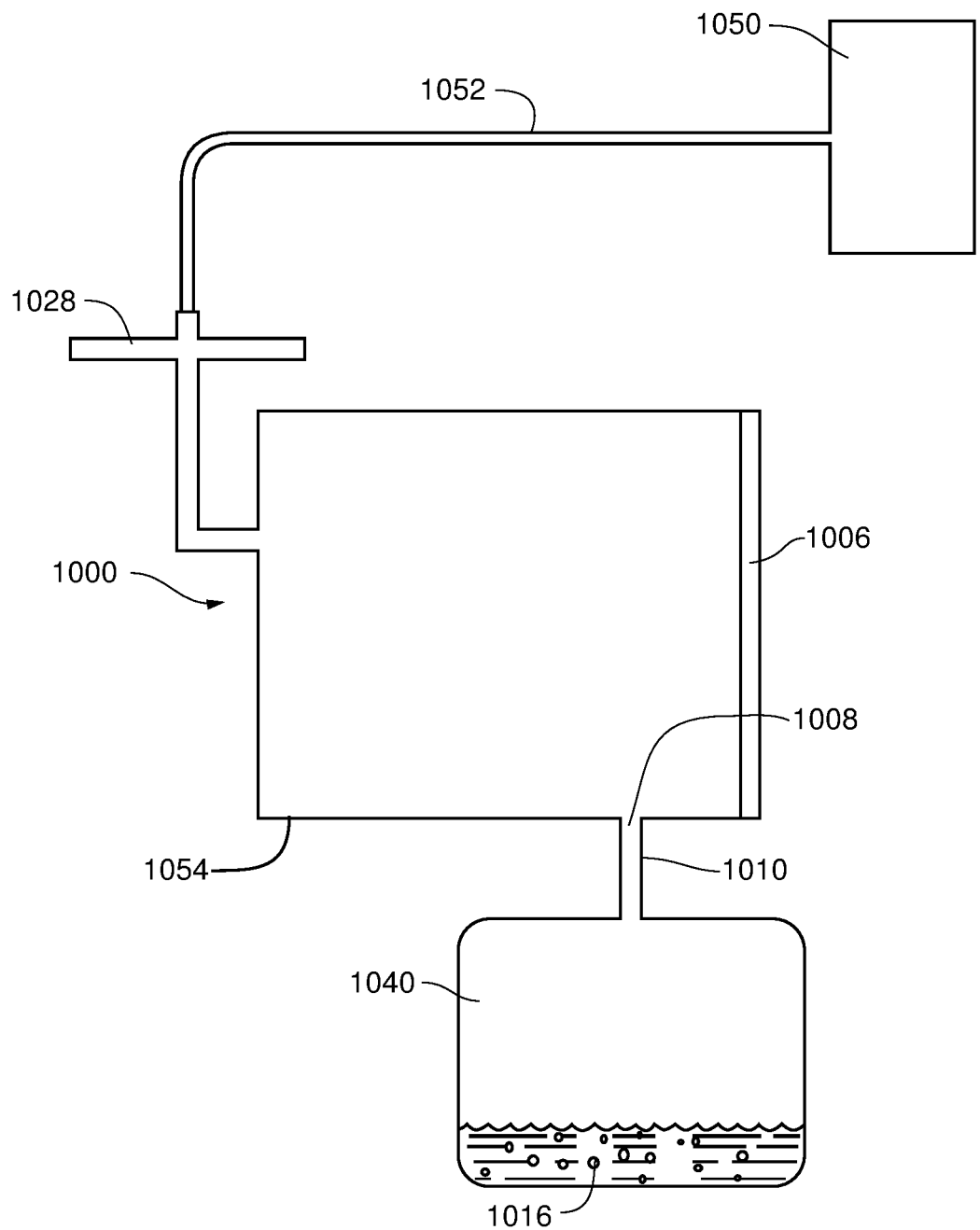
FIG. 2D shows a cross-sectional view of a gas permeable cell culture device after being oriented to a cell recovery position and after cells and residual media have been moved to a cell collection receptacle.

FIG. 2D shows how this is accomplished. Cell culture and cell recovery device 1000 is oriented in the cell removal position, media removal conduit 1010 is preferably connected to cell collection receptacle 1040 which replaces enclosed waste receptacle 1032, a gas delivery component is connected to vent 1028, such as diaphragm pump 1050 which is connected to vent 1028 by gas conduit 1052. When the gas delivery component is actively delivering gas (i.e. in this example when diaphragm pump 1050 is actuated), gas is delivered into gas conduit 1052, through vent 1028, and into cell culture and cell recovery device 1000. As gas is delivered into cell culture and cell recovery device 1000, residual media volume 1020B, containing suspended cells 1016, is displaced as it is driven into media removal opening 1008 which emanates from sidewall(s) 1054, out of cell culture and cell recovery device 1000 by way of media removal conduit 1010, and into cell collection receptacle 1040. Preferably, the cell collection receptacle 1040 is an enclosed container with a suitable design for whatever downstream processes it will be subjected to, such as centrifugation and/or cryopreservation. Preferably, in order to prevent damage to growth surface 1006, a growth surface support is present and holds growth surface 1006 in a planar state as gas enters cell culture and cell recovery device 1000.

Skilled artisans are encouraged to recognize that increasing the height at which the initial media volume resides above the bottom of the device is advantageous for a variety of reasons, including the ability to increase the source of nutrients, increase the sink for cellular waste products, and allow a greater portion of the initial media volume to be removed without cell loss. Although media height is not limited, preferably the media height as determined from the lowest portion of the media to the uppermost portion of the media when the growth surface and/or the uppermost surface of media is in a horizontal position is preferably within a range of 1 cm to 25 cm, more preferably within a range of 1 cm to 20 cm, even more preferably within a range of 1 cm to 15 cm, and even more preferably within a range of 2 cm to 11 cm. Although residual media height is not limited, preferably residual media height is within a range of 0.2 cm to 2.0 cm, more preferably, within a range of 0.2 cm to 1.0 cm, and even more preferably within a range of 0.2 cm to 0.5 cm as determined as determined from the lowest portion of the media to the uppermost portion of the media when the growth surface and/or the uppermost surface of media is in a horizontal position.

Figure 3:
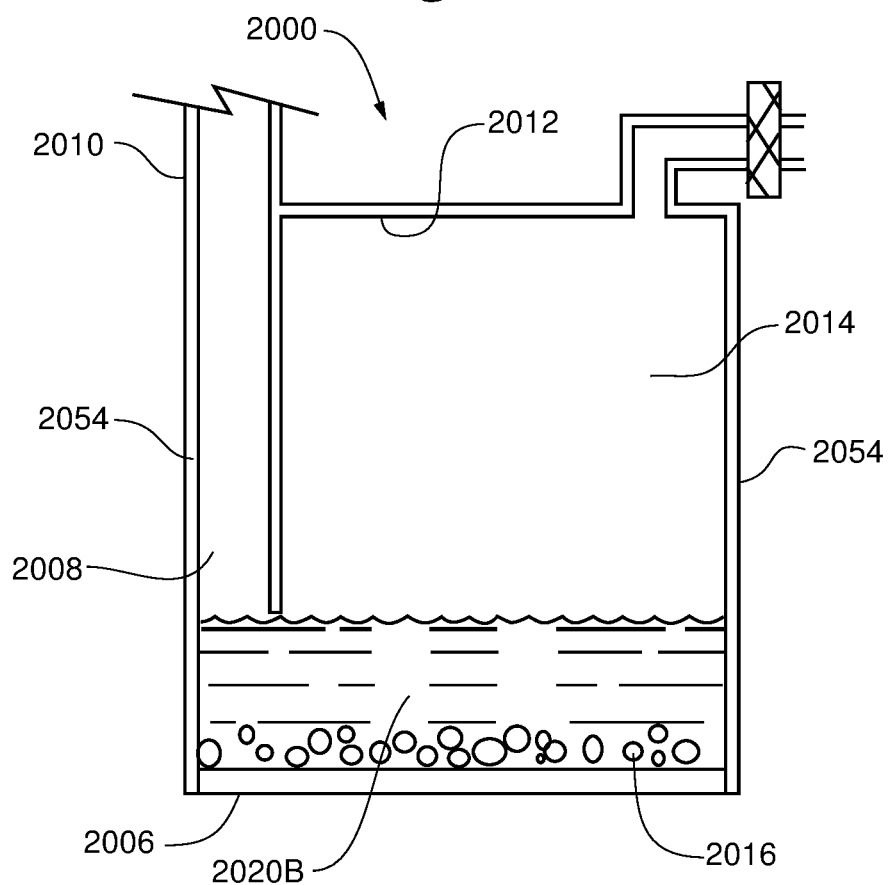
FIG. 3 shows a cross-sectional view of a gas permeable cell culture device with a media removal conduit and a media removal conduit opening.

FIG. 3 shows yet another embodiment of the present invention in which a cross-sectional view of cell culture and cell recovery device 2000 includes media removal opening 2008 located within media removal conduit 2010. Media removal conduit does not access internal volume 2014 by way of sidewall(s) 2054 and in this depiction moves through upper confine 2012. Media can be collected as previously described when cell culture and cell recovery device 2000 is oriented in the media collection position (i.e. the cell culture position) in which cells 2016 reside upon growth surface 2006. As shown in FIG. 3, a portion of the original media volume has been removed via media removal conduit 2010. Residual media 2020B resides at the height of media removal opening 2008. Cells 2016 can be collected as previously described by simply reorienting cell culture and cell recovery device 2000 to the cell removal position, in which media removal opening 2008 resides at a low point of residual media volume 2020B. With cells 2016 suspended in residual media 2020B, they can be collected by removing residual media volume 2020B via media removal conduit 2010.

Figure 4A:
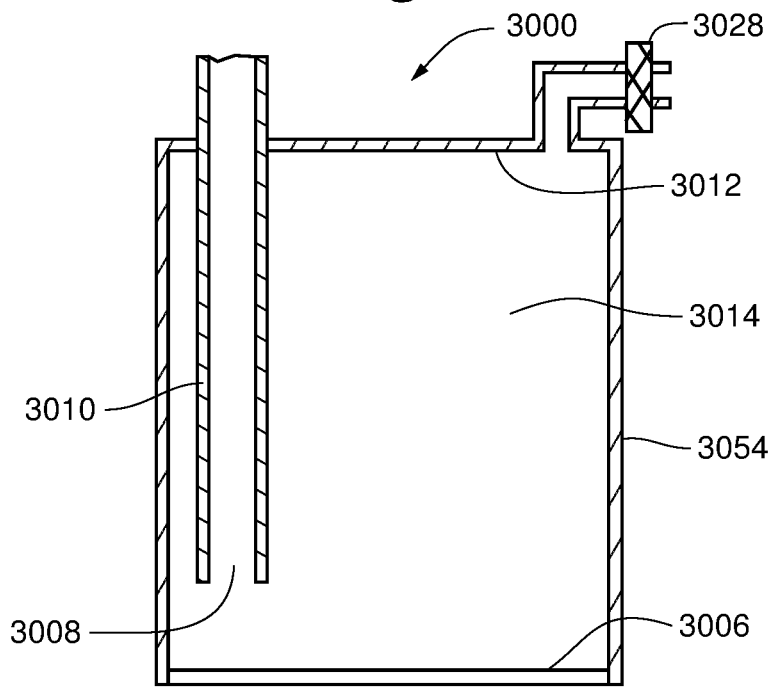
FIG. 4A shows a cross-sectional view of a gas permeable cell culture device with a media removal conduit and a media removal conduit opening positioned in a media removal location.

Another embodiment of the present invention allows the opening of a conduit to alter its distance from the growth surface. In FIG. 4A, a cross-sectional view of a cell culture and cell recovery device 3000 is shown in a cell culture position and in a state of static cell culture. Cell culture and cell recovery device 3000 comprises an internal volume 3014 bounded by an upper confine 3012, growth surface 3006, vent 3028, and media removal conduit 3010 with media removal opening 3008. Preferably upper confine 3012 is adjoined to growth surface 3006 by sidewall(s) 3054 and more preferably sidewall(s) 3054 are perpendicular to growth surface 3006 during the culture process.

Figure 4B:
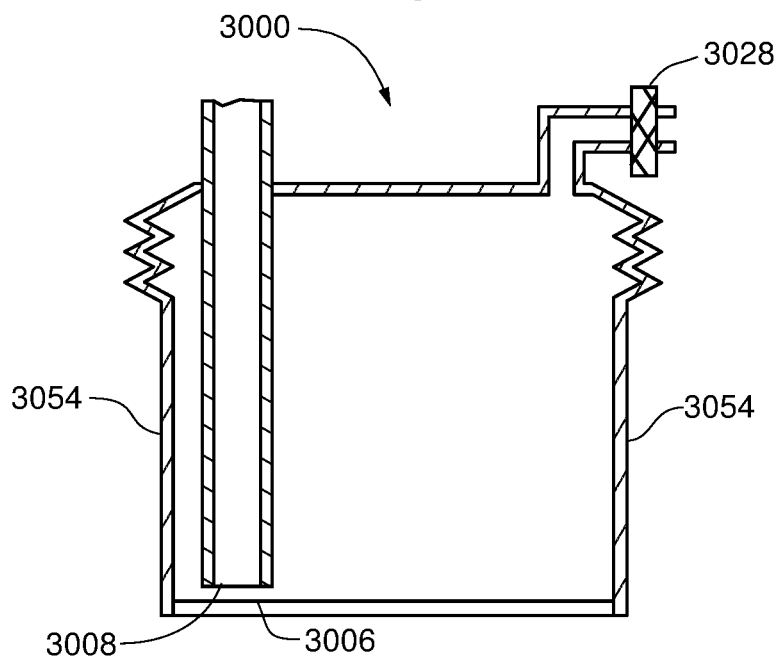
FIG. 4B shows a cross-sectional view of a gas permeable cell culture device with a media removal conduit and a media removal conduit opening positioned in a cell removal location.

Media can be removed via media removal opening 3008 in the manner previously described, preferably when cell culture and cell recovery device 3000 resides in a position in which planar growth surface 3006 resides in a horizontal position and cells reside upon the growth surface, not suspended in the media (i.e. not distributed within the media). After the media removal process is complete, fresh media can be added by causing vent 3028 to be open to ambient atmosphere (e.g. disconnecting or venting the gas conduit) and adding fresh media via media removal conduit 3010 (or any other port that may present in the in the device and appropriately structured for that purpose). If there is no need of adding fresh media into the device and the culture is to be terminated, cell removal can be undertaken. By configuring the cell culture and cell recovery device to include means for altering the distance between media removal opening 3008 and growth surface 3006, the location of media removal opening 3008 can be altered from a media removal position to a cell removal position. In so doing, not only can the media removal opening act to reduce the media volume without removing cells, as described previously, it can also remove residual media and cells after media volume has been reduced. In this manner, just one port can be used to concentrate the cells in residual media and also remove the concentrated cells. FIG. 4B shows one example of how to accomplish this. In this example, sidewall(s) 3054 provide structure connecting the lower boundary of the internal volume of the cell culture and cell recovery device to the upper confine. In this depiction, growth surface 3006 is the lower boundary. Sidewall(s) 3054 of cell culture and cell recovery device 3000 includes means to adjust the distance between media removal opening 3008 and growth surface 3006. Skilled artisans are encouraged to recognize there are many way of accomplishing this. For example, sidewall(s) 3054 can include flexible material such as silicone and be bellowed to allow the height of sidewall(s) 3054 to be altered. When the height of sidewall(s) 3054 is altered to move media removal opening 3008 from a media removal position to a cell removal position as shown, the distance between media removal opening 3008 and growth surface 3006 is reduced and media removal opening 3008 is placed in a cell removal position where it is in proximity of growth surface 3006 and is able to allow passage of residual media and cells. Stated differently, when cell culture and cell recovery device 3000 is in the media removal position, the distance between media removal opening 3008 and growth surface 3006, which in this depiction is the lower boundary upon which media can reside when the device is operating in a state of static cell culture, exceeds the distance between media removal opening 3008 and growth surface 3006 when in the cell removal position. Conversely, when cell culture and cell recovery device 3000 is in the cell recovery position, the distance between media removal opening 3008 and growth surface 3006 is less than the distance between media removal opening 3008 and growth surface 3006 when cell culture and cell recovery device 3000 is in the media removal position.

Skilled artisans are advised the ways to adjust the distance between the media removal opening and the growth surface are many and varied. For example, there are numerous ways to make the walls of the device capable of collapsing, including making them out of a flexible material, in a piston like manner where one section of the wall slides past the other in a liquid tight manner, and the like. In those cases, the distance between the upper confine of the cell culture and cell recovery device and the growth surface will be reduced as the media removal opening is altered from a media removal position to a cell removal position. However, skilled artisans are advised to recognize that altering the distance between the upper confine of the cell culture and cell recovery device and the growth surface is not the only way to move the media removal opening from a media removal position to a cell removal position.

Figure 5A:
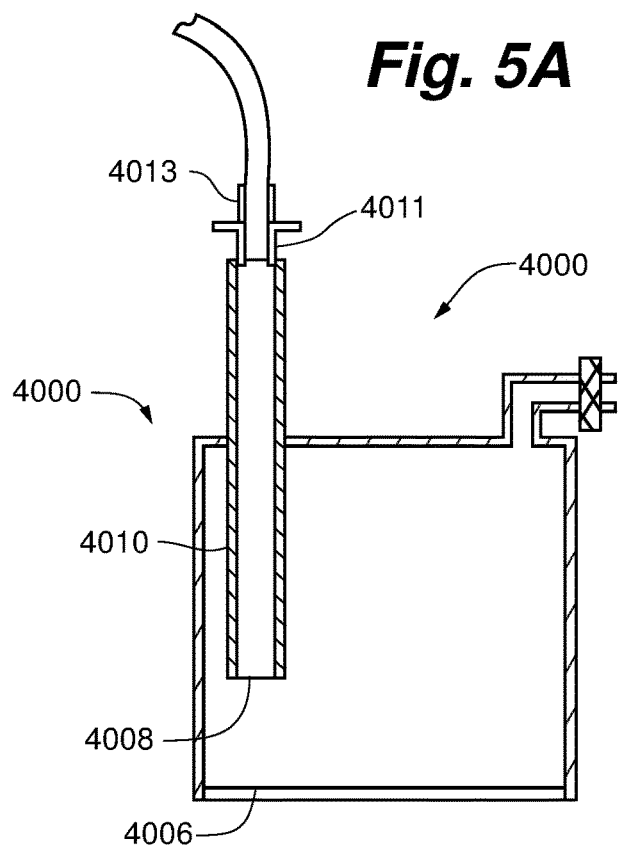
FIG. 5A shows a cross-sectional view of a gas permeable cell culture device with a media removal conduit and a media removal conduit opening positioned in a cell removal location.
Figure 5B:
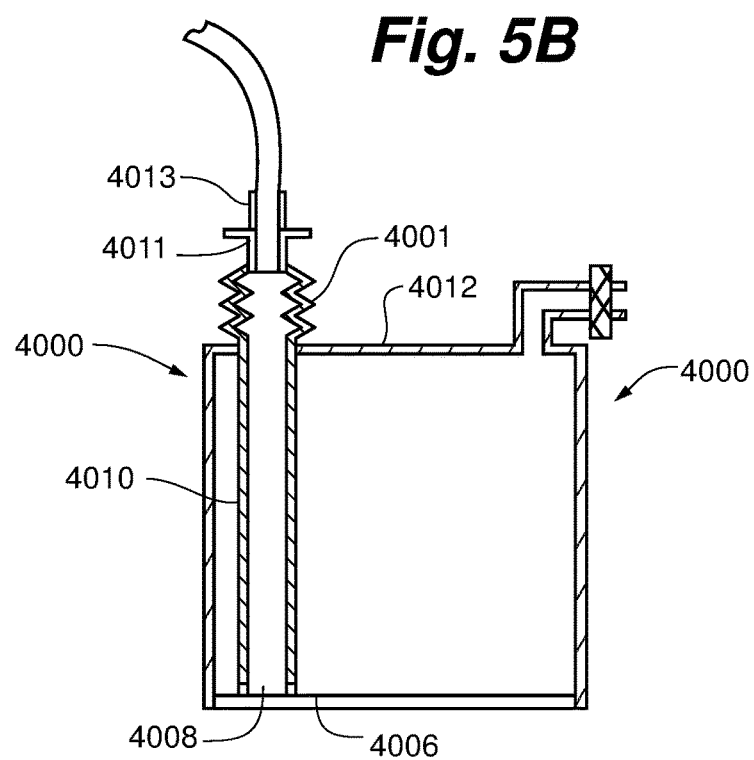
FIG. 5B shows a cross-sectional view of a gas permeable cell culture device with a media removal conduit and a media removal conduit opening positioned in a cell removal location.

FIG. 5A and FIG. 5B show a cross-sectional view of cell culture and cell recovery device 4000 configured to adjust the distance between media removal opening 4008 and growth surface 4006. Flexible shroud 4001 forms a seal against media removal conduit 4010 and upper confine 4012. Media removal conduit 4010 has a sealed joint, which in this illustrative example is comprised of female luer fitting 4011 that interfaces with male luer fitting 4013, thereby allowing collection vessels to be easily attached to media removal conduit 4010. Skilled artisans are encouraged to recognize there are many ways to make such a connection including sterile tubing welds. To alter the distance between media removal opening 4008 and growth surface 4006, the height of flexible shroud 4001 is altered. FIG. 5B shows the height of flexible shroud 4001 after a force has been applied to its upper surface in order to diminish its height (i.e. compressing the bellows in the direction of growth surface 4006), thereby moving media removal opening 4008 in the direction of growth surface 4006 and reducing the distance between media removal opening 4008 and growth surface 4006. Skilled artisans are encouraged to recognize that a variety of distances between media removal opening 4008 and growth surface 4006 become possible without putting cell culture and cell recovery device 4000 at risk of contamination. Preferably, during cell recovery, media removal opening 4008 is adjacent to growth surface 4006, and cell culture and cell recovery device 4000 is in the cell culture position (i.e. growth surface 4006 is in a horizontal position). This facilitates automated processing in a manner that does not require the cell culture and cell recovery device to be rotated from its cell culture position to remove media and cell contents of the cell culture and cell recovery device.

Prior to the collection of cells, it may be helpful to agitate the device to dislodge cells from the growth surface and suspend them into the media. We have discovered that non-adherent cells such as T cells, even when the growth surface is a hydrophobic membrane such as silicone, have a tendency to remain piled upon the growth surface when the device is tilted. Thus, to ensure cells are not left in the device when the residual media is removed, agitating the device is preferred. For example, one may simply swirl the residual media about and visually determine the cells have dislodged from the growth surface and moved into the residual media. Once cells are dislodged from the growth surface, collection of cells can be accomplished by traditional methods of withdrawing the media and cells (such as by use of a peristaltic pump). Withdrawing cells by drawing the media out of the device will cause the gas permeable membrane to move from a horizontal position as a vacuum forms in the device. So long as the integrity of the membrane is not breached, this can be done. However, a preferred method that does not put the membrane at risk of damage, is to use the gas displacement method previously described to recover the cells.

Figure 5C:
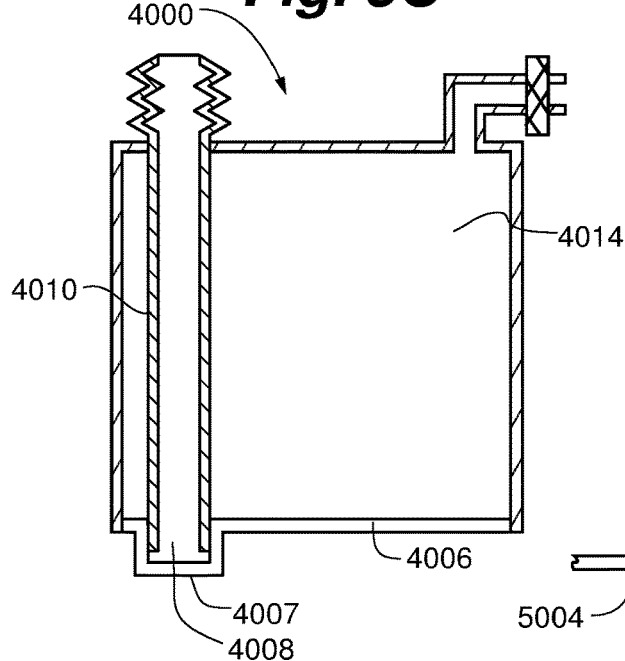
FIG. 5C shows a cross-sectional view of a gas permeable cell culture device with a media removal conduit and a media removal conduit opening positioned in a cell removal location and where the cell removal conduit opening resides in a pocket of the growth surface.

FIG. 5C shows cell culture and cell recovery device 4000 configured to further assist automated cell collection by eliminating the need to tilt the device to place the conduit opening being used to collect cells at the lowest position within the device. When growth surface 4006 resides in the preferred horizontal plane for cell culture, cell collection pocket 4007 resides below the horizontal plane of growth surface 4006. Media removal opening 4008 resides within cell collection pocket 4007. In this position, media removal opening 4008 resides at the low point of internal volume 4014 (i.e. the lowermost location of media when the device is oriented for a state of static cell culture), facilitating recovery of media and cells. This feature can be present in any cell culture and cell recovery device embodiment.

In general, when media removal opening is in the media removal position, it preferably does not have the ability to remove all contents of the cell culture and cell recovery device. This ensures at least a portion of media and the majority of cells remain in the device even if the gas delivery component becomes defective, or fails to be stopped from delivering gas, and continues to deliver gas into the device after all the media that can possibly move through the media removal opening has done so.

If one seeks to avoid designing the cell culture and cell recovery device in a manner that alters the distance between the media removal opening and the growth surface, or requires a large angle of rotation to collect cells, it is easy to create a distinct media removal opening and a distinct cell removal opening and apply the process previously described to simplify downstream processing without fear of cell loss or damage to the growth surface and/or the gas permeable material. FIG. 6A, FIG. 6B, FIG. 6C, and FIG. 6D provide such an example. A cross-sectional view of a cell culture and cell recovery device 5000 is shown a static cell culture position comprising an internal volume 5014 bounded by an upper confine 5012, a lower boundary which in this depiction growth surface 5006, vent 5028, media removal conduit 5010 with media removal opening 5008, and cell removal conduit 5004 with cell removal opening 5002. Preferably upper confine 5012 is adjoined to the lower boundary by sidewall(s) 5054 and more preferably sidewall(s) 5054 are perpendicular to the growth surface. An initial media volume 5020A is present in the device. Initial media volume 5020A resides at an initial media height 5021A, which is equal to the distance from the highest media level to the lowest media level. In use, cells 5016 reside on growth surface 5006. In general, skilled artisans should be aware that non-adherent cells (i.e. also called suspension cells) may not all touch the growth surface since they will be able to pile upon each other with the lower most cells in actual physical contact with the growth surface. Growth surface 5006 is preferably oriented in a horizontal position during the culture process, is preferably comprised of non-porous liquid impermeable material, and is preferably hydrophobic in the case where non-adherent cells are to be cultured. Cells 5016 are at an initial cell density, which is the quantity of cells 5016 divided by the initial media volume 5020A (e.g. cells/ml), and cells 5016 are also at an initial surface density, which is the quantity of cells 5016 divided by the surface area of growth surface 5006 upon which cells reside (e.g. cells/cm$^2$). Again, in the case of non-adherent cells this includes the total number of cells that have gravitated to a state of rest and which are prevented from further gravitation by the growth surface. This includes those cells that have come to rest upon other cells, some of which are not in direct contact with the growth surface. Media removal opening 5008 resides a distance from growth surface 5006 and as will be seen, the distance also constitutes residual media height 5021B.

Figure 6A:
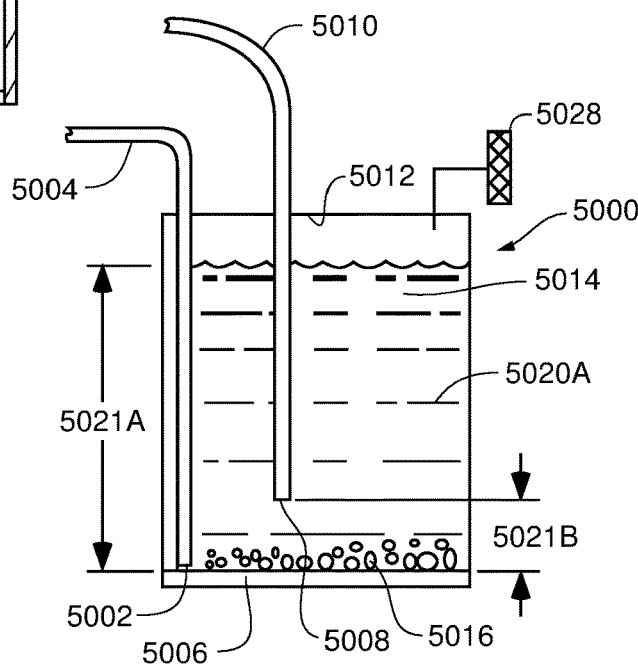
FIG. 6A shows a cross-sectional view of a gas permeable cell culture device with a media removal conduit and a cell removal conduit.
Figure 6B:
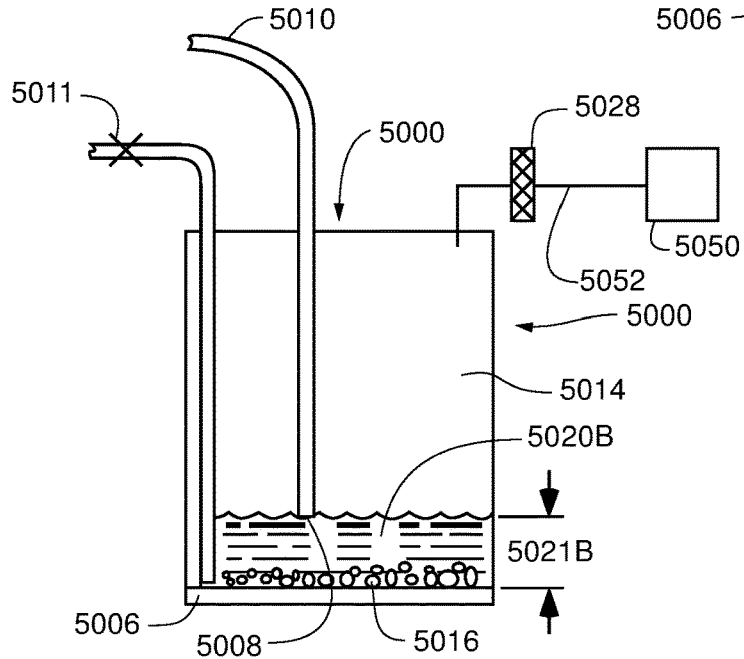
FIG. 6B shows a cross-sectional view of a gas permeable cell culture device after gas has been pushed into the device and media has been removed via the media removal conduit.
Figure 6C:
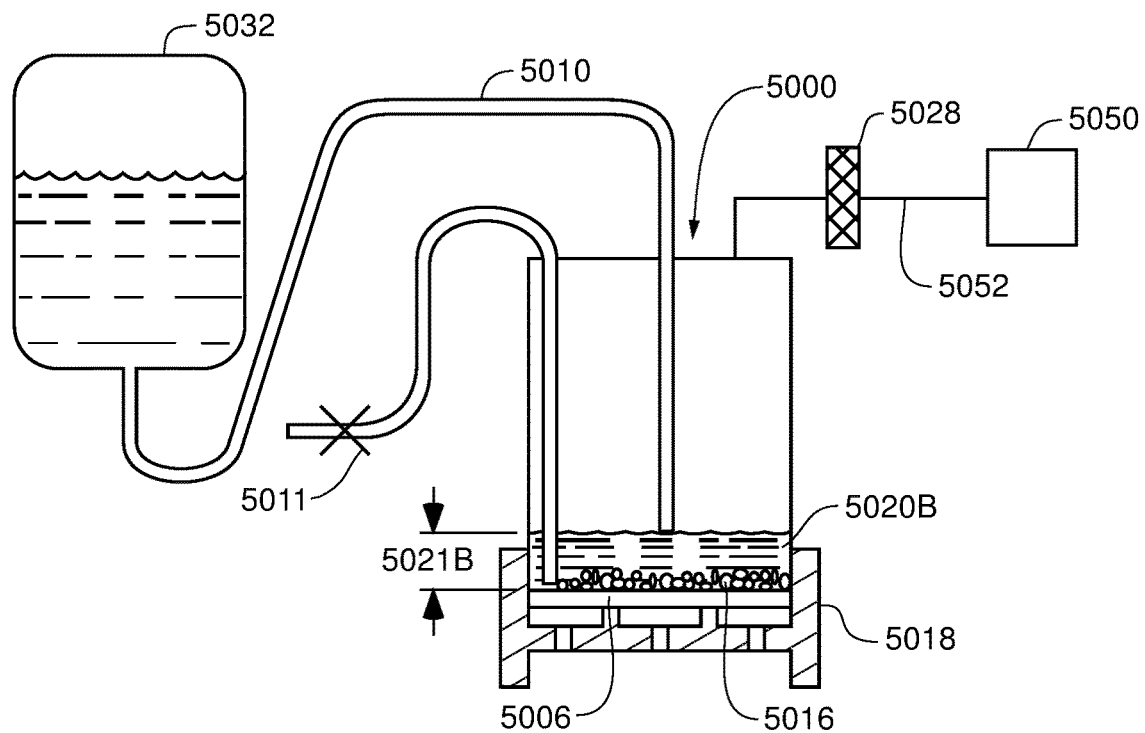
FIG. 6C shows a cross-sectional view of a gas permeable cell culture device after gas has been pushed into the device and media has been removed via the media removal conduit and moved into a waste collection receptacle.

At some point in the cell culture process, performing a media removal process that reduces initial media volume 5020A to a smaller residual media volume in order to either add fresh media or concentrate the cells in the residual media volume becomes desirable. To remove a portion of initial media volume 5020A, a gas delivery component is connected to vent 5028 as best shown in FIG. 6B. In this example, the gas delivery component is diaphragm pump 5050 which is connected to vent 5028 by gas conduit 5052. When diaphragm pump 5050 is actuated, it drives gas into gas conduit 5052, through vent 5028, and into cell culture and cell recovery device 5000. As gas is driven into internal volume 5014 of cell culture and cell recovery device 5000, a portion of initial media volume 5020A is displaced and is driven into media removal opening 5008, through media removal conduit 5010 and out of cell culture and cell recovery device 5000 into a waste receptacle, leaving residual media volume 5020B and cells 5016 as shown in FIG. 6C. Residual media volume 5020B resides at residual media height 5021B, defined as the distance between the uppermost residual media location and the lowermost residual media location. Cells 5016 are at a residual cell density, which is the quantity of cells 5016 divided by residual media volume 5020B (e.g. cells/ml), and cells 5016 are also at residual surface density 5017B, which is the quantity of cells 5016 divided by the surface area of growth surface 5006 upon which cells reside (e.g. cells/cm$^2$). The waste receptacle need not be an enclosure and need not be physically attached to media removal conduit 5010. For example it could instead be something as common as a laboratory sink, but preferably the waste receptacle is an enclosed container such as a bag or centrifuge tube and is connected in a sealed manner to media removal conduit 5010 in order to isolate potential biohazards and/or maintain sterility in a closed system manner. Such an enclosed container is represented in FIG. 6C as enclosed waste receptacle 5032 which is attached to media removal conduit 5010. As a portion of initial media volume 5020A is being removed from cell culture and cell recovery device 5000, the volume of media in waste receptacle 5032 is initial media volume 5020A less the portion of initial media volume 5020A within media removal conduit 5010 (if any). Preferably during this media removal process, growth surface 5006 is prevented from moving in the opposite direction from upper confine 5012 without constraint as gas enters cell culture and cell recovery device 5000 and the pressure of internal volume 5014 elevates. As shown in FIG. 6C, this is accomplished by growth surface support 5018, which makes contact with growth surface 5006 and holds growth surface 5006 in a substantially planar position to prevent damage to the growth surface. The term substantially has been previously described as it relates to a horizontal position and this also applies to a planar position. Skilled artisans are advised to consult co-pending '814 and '848 for further guidance related to the growth surface support design.

Figure 6D:
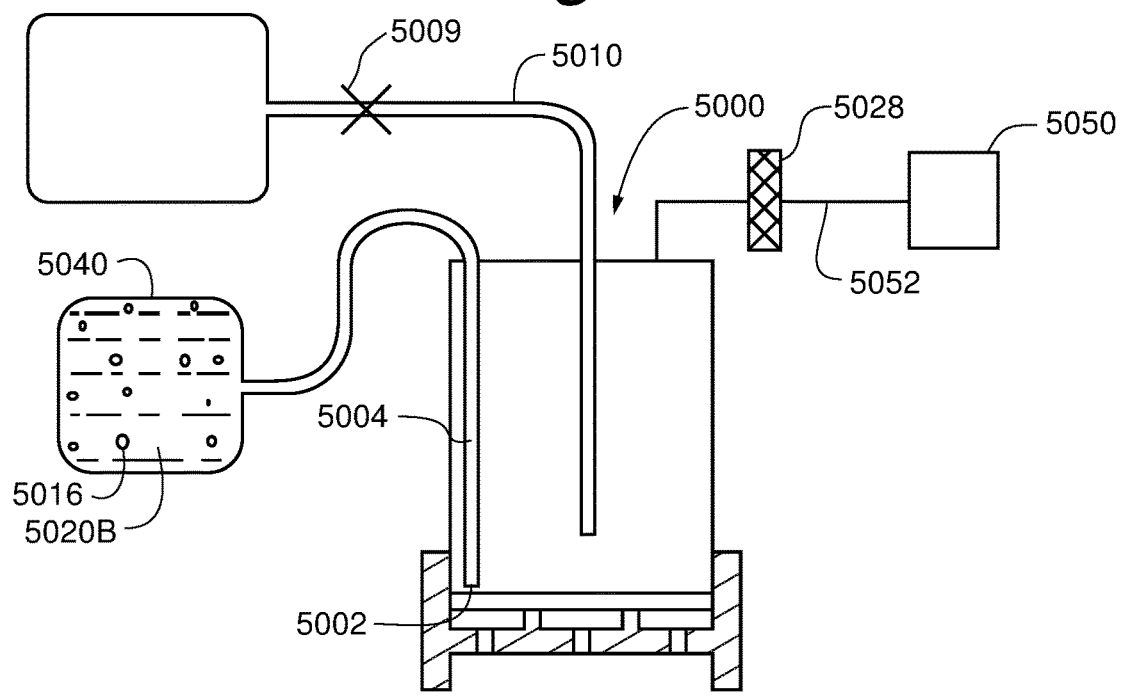
FIG. 6D shows a cross-sectional view of a gas permeable cell culture device after gas has been pushed into the device and cells and a residual volume of media have be removed via a cell removal conduit and moved into a cell collection receptacle.

Referring to FIG. 6D, to recover cells 5016, a further step is undertaken in which cell collection receptacle 5040 is attached to the cell removal conduit 5004 of the cell culture and cell recovery device 5000 and media removal conduit 5010 is blocked from fluid flow by closed media removal conduit clamp 5009. Blocking media removal conduit 5010 from fluid flow may be as simple as use of a hemostat, or may be automated as will be described further into this disclosure. As previously described, prior to the collection of cells it may be helpful to agitate the residual media within the device to dislodge cells from the growth surface and suspend them into the residual media. Although collection of cells can be accomplished by traditional methods of withdrawing the media and cells (such as by use of a peristaltic pump), the preferred method is to prevent the growth surface and/or gas permeable material from moving toward the upper confine and distorting in shape during this process by use of the positive pressure the gas displacement method provides. As shown in FIG. 6D a gas delivery component is connected to vent 5028 by way of gas conduit 5052. In this example, the gas delivery component is diaphragm pump 5050. When diaphragm pump 5050 is actuated, it drives gas into gas conduit 5052, through vent 5028, and into the cell culture and cell recovery device 5000. As gas is driven into cell culture and cell recovery device 5000, residual media 5020B and cells 5016 are displaced and driven into cell removal opening 5002, through cell removal conduit 5004, and into cell collection receptacle 5040. Cell collection receptacle 5040 can then be removed, preferably in a sterile manner such as by way of a sterile tubing weld, for subsequent processing of cells 5016.

It is possible a rinse of a portion of the internal volume cell culture and cell recovery device may be desired to collect any cells that may remain in the device after the initial cell removal process. For example, this can be accomplished without need to add a source of liquid that was not present in the device at the onset of the cell removal process. One could do so by simply using the media residing in the enclosed waste receptacle as the rinse material. To do so, the media removal clamp would be opened, the vent would be opened, and the waste receptacle would be pressurized such as by simply elevating it to whatever height is needed to allow media to flow back into the device. This can be assisted by squeezing the waste receptacle if it is flexible, such as a bag, to initiate flow into the device. When a user determines an adequate amount of media has been returned to the device, the media removal conduit clamp can be closed and the cell removal process can be repeated Although the described process of using air to displace media and/or cells can be undertaken in a simple manner such as by opening and closing conduits with a hemostat and turning the gas delivery component on and off by visual assessment of the process, automating aspects of the process can be beneficial in the case where many cell preparations are desired. One of the factors to consider is the prospect of the gas delivery component continuing to deliver gas to the device after media and/or cells have been driven into their respective receptacles. In this case, gas would be driven into the receptacles and the receptacles would be pressurized, potentially causing them to breach their seal. Furthermore, gas could cause damage to the cells as the surface tension of bubbles and gas/cell contact may disrupt the integrity of the cell membranes. Another factor to consider is the pressure that can build within the cell culture and cell recovery device itself when the gas delivery component is not turned off after media and/or cells are driven to their respective receptacles.

Figure 7:
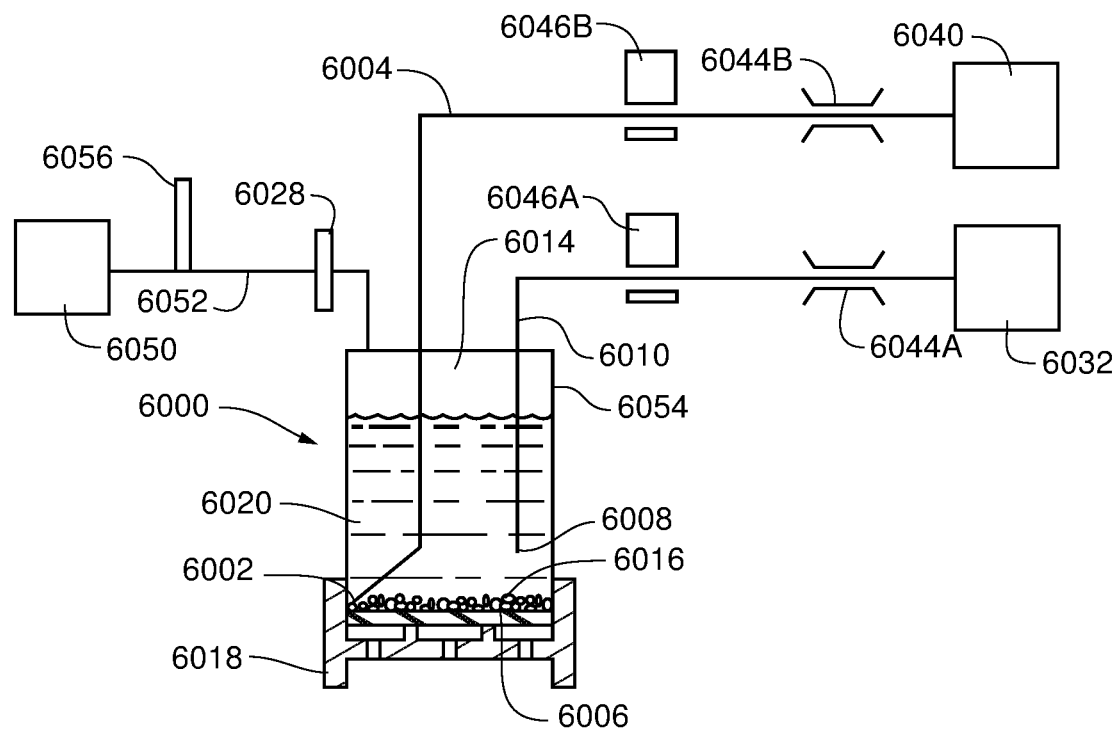
FIG. 7 shows a schematic view of a gas permeable cell culture device interfacing with equipment to automate the removal of media and cells.

FIG. 7 shows a schematic of an illustrative embodiment of system designed to resolve these problems. Skilled artisans are encouraged to recognize this illustrative embodiment is compatible with a cell culture and cell recovery device configured with just one media removal conduit as for example shown in FIG. 3, an adjustable media removal conduit, or separate media and cell removal conduits. In general, the automation system preferably recognizes the point in the process when media exiting the cell culture and cell recovery device via a media removal conduit or a cell removal conduit is replaced by gas. Referring again to FIG. 7, fluid detection components 6044A and 6044B are capable of recognizing the point in the process when media exiting the cell culture and cell recovery device via a media removal conduit or a cell removal conduit is replaced by gas and are in proximity of media removal conduit 6010 and cell removal conduit 6004. Stated differently, the fluid detection components are able to determine if liquid or gas resides in the conduits. First flow control component 6046A acts to open or close the media removal conduit 6010 and second flow control component 6046B acts to open or close cell removal conduit 6004. In this example, electronically actuated pinch clamps act as the flow control components and the conduits are made of flexible tubing. Cell culture and cell recovery device 6000 is preferably a static cell culture device in its cell culture position (i.e. media is not subject to forced mixing and the growth surface is below the upper confine and is preferably in the horizontal position). Media 6020 resides at a first media volume and at a first media height within cell culture and cell recovery device 6000 and cells 6016 have settled upon growth surface 6006 due to gravity. Growth surface 6006 is preferably held in a horizontal plane by growth surface support 6018. The distance from media removal opening 6008 to growth surface 6006 exceeds the distance from cell removal opening 6002 to growth surface 6006.

Preferably, the cell removal conduit is in contact with a sidewall, is in contact with the growth surface, is positioned along the edge where sidewall(s) 6054 interface(s) with the growth surface, or in a pocket within the growth surface as previously described, thereby positioning the cell removal opening for maximum cell recovery. Gas conduit 6052 connects vent 6028 to gas delivery component 6050. Media removal conduit 6010 is connected to waste receptacle 6032 and cell removal conduit 6004 is attached to cell collection receptacle 6040. A software algorithm is able to deliver the electronic signals needed to perform the various tasks needed to collect cells in a highly concentrated state. To reduce the volume of media 6020, flow control component 6046A is placed in a state that does allow fluid flow through media removal conduit 6010 and flow control component 6046B is placed in a state that does not allow fluid flow through cell removal conduit 6004, the gas delivery component is actuated and gas enters cell culture and cell recovery device 6000 via vent 6028, pressurizing internal volume 6014 and driving media 6020 into media removal opening 6008, through media removal conduit 6010, and into waste receptacle 6032. When the height of media 6020 has reached a level that is just a miniscule distance below at the height of media removal opening 6008, gas enters media removal opening 6008, is driven through media removal conduit 6010, and is detected by fluid detection component 6044A. Fluid detection component 6044A sends a signal notifying flow control component 6046A to stop fluid flow to waste receptacle 6032. Preferably gas delivery component 6038 is simultaneously terminated from delivering gas and/or opens pressure relief valve 6056. Although this step is optional, the advantage is to minimize pressure build up in cell culture and cell recovery device 6000 and skilled artisans are encouraged to recognize there are numerous ways to achieve that objective including use of a gas delivery component that cannot deliver gas after a specific pressure threshold is reached, use of a pressure relief valve, and the like. Once media 6020 flow to waste receptacle 6032 is terminated, the operator can then make a determination as to whether or not to agitate the residual amount of media in order to dislodge cells 6016 from growth surface 6006. Skilled artisans are encouraged to recognize that a robust system will allow the operator to override the automation and stop the media flow to the waste receptacle on command (e.g. as may be needed if cells are being lost into the waste receptacle).

Once the operator has determined that cells 6016 are in a suitable state of suspension within the residual amount of media 6020 and/or the cell recovery process should commence, the user presses a button and the process resumes. Internal volume 6014 is pressurized and flow control component 6046B is actuated to allow fluid flow to cell collection receptacle 6040. Cell culture and cell recovery device 6000 may or may not be oriented into a position to allow all the media and cells to collect at a low point at this time, depending on operator preference and whether or not the cell culture device is designed to place the cell removal conduit in a position of maximum cell recovery when the device is oriented in the static cell culture position. Skilled artisans will recognize the steps of agitation to dislodge cells and orienting the device into a position of maximum cell recovery can also be automated. When in the static cell culture position, maximum cell recovery can be obtained when cell removal opening 6002 is located below the height of growth surface 6006. For example, by a pocket in the growth surface as previously described, a moat such as a relieved area around the perimeter of the growth surface where the bottom of the moat is lower than the growth surface, or any feature that could act to allow media to reside at a height below the growth surface and become a collection location for the cell removal opening. At some point in the automated cell removal process, gas enters cell removal opening 6002, travels through cell removal conduit 6004, and is detected by fluid detection component 6044B. At that point, fluid detection component 6044B sends a signal causing flow control component 6046B to terminate fluid flow to cell collection receptacle 6040. At this point, receptacle 6040 can be removed, preferably in a sterile manner by use of a sterile tubing welder. However, if the operator determines an additional rinse of the growth membrane can be useful in collecting more cells, such that any that may have remained within the device, that process becomes easily possible. Flow control component 6046A can be placed in a state where fluid flow through media removal conduit 6010 is not blocked, but instead is open, and waste receptacle 6032 is simply elevated or squeezed (preferably the waste receptacle is a bag) in order to drive media 6020 from waste receptacle 6032 into cell culture and cell recovery device 6000. Preferably vent 6028 is open to atmosphere during this step. Once an appropriate volume of media 6020 is delivered back into cell culture and cell recovery device 6000, the cell recovery process can be repeated. This step of adding and removing media can be repeated as necessary to collect as many cells as the operator deems appropriate.

The method of using a device of the embodiment shown in FIG. 7 would be such that the gas delivery component is connected to a filter that is connected to the gas permeable cell culture and cell recovery device containing media and cells wherein the cell culture device includes a media removal conduit, connecting the first fluid detection component to the media removal conduit, connecting the first fluid flow control component to the media removal conduit, initiating gas delivery from gas delivery component, whereby initiating can be use of any process or equipment that causes gas to move into the cell culture device and wherein the gas displaces media from the cell culture device into a media collection vessel connected to the media removal conduit. The first fluid detection component determines when the fluid that is moving through the media removal conduit has changed from liquid to gas and the first fluid detection component sends a signal to the first fluid flow control component and upon receiving the signal the first flow control component terminates the flow of fluid through the media removal conduit. After the first flow control component has terminated the flow of fluid through the media removal conduit, an option of performing agitation of the media is to dislodge cells from the growth surface into the residual media can be undertaken. The cell culture device can also be oriented into a new position wherein media is in contact with said a cell removal conduit. However, if the growth surface remains in the horizontal position and the cell removal opening of the cell removal conduit is in contact or proximity of the growth surface, such a step of reorienting the device need not be undertaken. A cell collection vessel is connected to the cell removal conduit, the second flow control component opens the flow of fluid through the cell removal conduit, gas from the gas delivery component moves into the cell culture device, media and cells move through the cell removal conduit into a cell collection vessel, the second fluid detection component determines when the fluid that is moving through the cell removal conduit has changed from liquid to gas and sends a signal to a second fluid flow control component. Upon receiving the signal, the second flow control component terminates the flow of fluid through the cell removal conduit.

Skilled artisans are encouraged to recognize that the device described in the illustrative embodiment of FIG. 7 can be simplified if it were to interface with a cell culture and cell recovery device of the type with just one media conduit that acts to reduce media volume and acts to remove residual media volume and cells. Such a device is described in further for example detail in FIGS. 2A-2D, 3, 4A-4B, 5A-5B and related text. Thus, the device can be simplified in include a gas delivery component that is capable of connecting to a filter that is connected to a gas permeable cell culture device, the gas delivery component capable of delivering gas into said gas permeable cell culture device by way of said filter, a first fluid detection component that is capable of determining when the type of fluid moving within a media removal conduit that is connected to a gas permeable cell culture device changes from liquid to gas, the component capable of sending a signal to a first fluid flow control component that is capable of terminating fluid flow through said media removal conduit. After the first flow control component has terminated the flow of fluid through the media removal conduit, if need be the cell culture device is oriented into a new position wherein media is in contact with the media removal conduit, a cell collection vessel is connected to the media removal conduit, first flow control component opens the flow of fluid through the media removal conduit, gas from said gas delivery component moves into said cell culture device, media and cells move through the media removal conduit into the cell collection vessel, the first fluid detection component determines when the fluid that is moving through the media removal conduit has changed from liquid to gas and sends a signal to the first fluid flow control component. Upon receiving the signal the first flow control component terminates the flow of fluid through said media removal conduit.

Skilled artisans will recognize that it is beneficial for cells to move out of the cell removal conduit and into the cell collection receptacle to the maximum extent practical. Thus, when automation is used in the manner shown in FIG. 7, by positioning the fluid detection component downstream from the flow control mechanism and as near to the receptacle as possible, the amount of media in the conduit at the time the flow control mechanism terminates flow will be limited to that between the position of the fluid detection component and the cell collection receptacle. Also, minimizing tubing inner diameter can further reduce the number of cells in the conduit. Alternatively, after gas is detected in a conduit, a small amount of additional gas can be driven through conduit(s) to ensure liquid is not trapped in the conduit(s) when the process is complete. This may be useful to ensure all cells are moved into the cell collection receptacle and/or allow sterile tubing splicing without liquid in the conduits. Alternatively, gas can be driven through the conduit to ensure liquid is not trapped in the conduit when the process is complete.

Skilled artisans are encouraged to recognize that the use of flow control components and fluid detection components are a convenience, but the cell recovery process can be undertaken manually. In a manual cell recovery process, an operator cold clamp flow through the cell removal conduit and open flow through the media removal conduit, and then could use a syringe to inject gas into the device until the gas is moved into the media removal conduit. Then the media can be agitated out of a state of quiescence as needed to dislodge cells from the growth surface. With the media removal conduit closed and the cell removal conduit open, gas is added into the device thereby driving cells and residual media out of the device.

Figure 8:
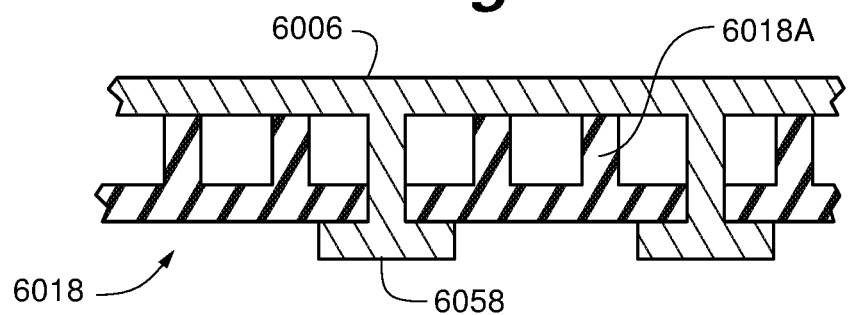
FIG. 8 shows a cross-sectional view of a growth surface interlocked into a growth surface support.
Figure 9:
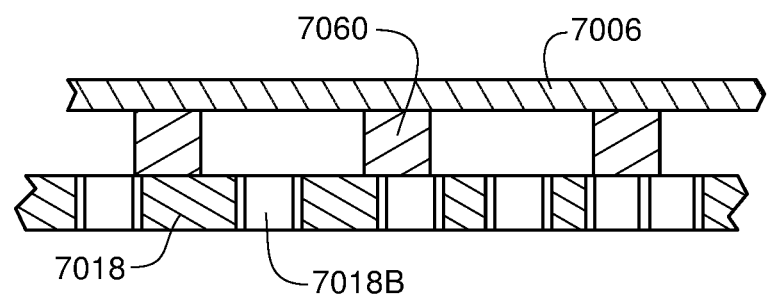
FIG. 9 shows a cross-sectional view of a growth surface molded onto a growth surface support.

Although the use of gas to displace media in order to prevent distortion of the growth surface and/or gas permeable material is an elegant approach, the device can be configured to minimize distortion growth surface and/or gas permeable material if one desires to withdraw media and/or cells from the device as opposed to displacement by gas as previously described. Such an approach can take place with the internal volume of the device at a pressure that is less than the pressure external to the device, thereby creating a pressure differential across the walls of the device. One approach to preventing distortion of the growth surface out of a planar state under such conditions is to physically attach the gas permeable material to a component (such as for example the growth surface support component). FIGS. 8 and FIG. 9 provide two such examples. For simplicity, the entire cell culture and cell recovery device is not shown. In FIG. 8, growth surface 6006 includes tabs 6058 emanating from its lower surface. Tabs 6058 interlock with mating features on growth surface support 6018. Vertical supports 6018A project from the base of growth surface support 6018 to hold growth surface 6006 in a horizontal position during static cell culture. Preferably, growth surface 6006 is comprised of a gas permeable material. In the case of silicone, the membrane can be fabricated by liquid injection molding and tabs 6058 can be molded into the membrane. FIG. 9 shows another example of maintaining the growth surface in a substantial planar state when pressure external to the growth surface exceeds that of the internal volume of the cell culture and cell recovery device. In this illustrative example, growth surface 7006 is comprised of silicone, which is over-molded onto grid 7060 (i.e. attached to the grid) which is attached to growth surface support 7018. Gas access openings 7018B allow passive gas exchange of the culture. Stated differently, ambient gas makes contact with the growth surface without need of being forced to do so. Thus, growth surface 7006 is held in place via the contact points with growth surface support 7018 even when pressure external to the growth surface exceeds that of the internal volume of the cell culture and cell recovery device.

Figure 10:
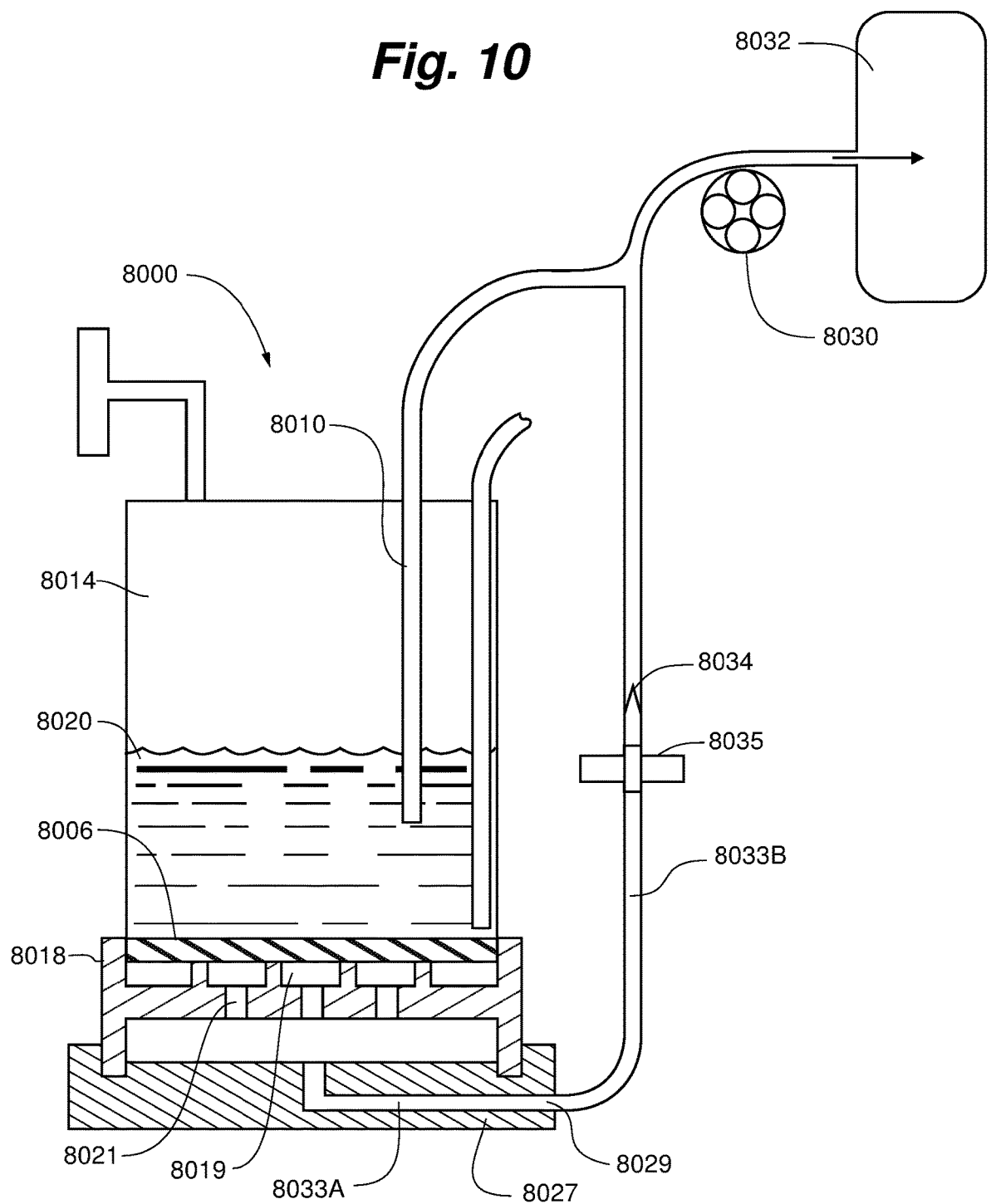
FIG. 10 shows a cross-sectional view of a gas permeable cell culture device and a process by which the growth surface remains in a planar position during media and cell removal.

Another way of maintaining the growth surface in a substantially planar state when media and/or fluid is drawn from the device is to balance the pressure external to the growth surface with that of the internal volume of the cell culture and cell recovery device. FIG. 10 shows an illustrative example of how that can be accomplished. Cell growth and cell recovery device 8000 includes growth surface support 8018. Growth surface support 8018 includes gas access opening(s) 8021. Gas access opening(s) allows passive movement of ambient gas to and from growth surface 8006, which is preferably liquid impermeable, gas permeable, non-porous, and residing in a substantially horizontal plane during cell culture. Stated differently, by passive movement the ambient gas makes contact with the gas permeable growth surface without any mechanism to physically force gas into contact with the gas permeable material. Media removal conduit 8010 is attached to waste receptacle 8032 and interfaces with a peristaltic pump 8030 in a manner such that peristaltic pump 8030 is able to draw media 8020 out of cell growth and cell recovery device 8000. During media removal, the ability of gas access opening(s) 8021 to communicate with ambient gas is minimized and preferably eliminated. In this depiction, liquid removal adapter 8027 is temporarily attached while the volume of media is reduced and mates with growth surface support 8018 and includes a pressure balance conduit 8033A, which further includes pressure balance conduit interface 8029, as for example may be a luer interface. Pressure balance conduit 8033A can mate to pressure balance conduit 8033B. Pressure balance conduit 8033B can also be attached to media removal conduit 8010 so that peristaltic pump 8030, when actuated, can draw gas from the space between liquid removal adapter 8027 and growth surface support 8018, in effect placing gas space 8019 at a reduced pressure relative to ambient gas. Preferably, if pressure balance conduit 8033B is attached to media removal conduit 8010, pressure balance conduit 8033B optionally includes check valve 8034 and/or pressure balance conduit filter 8035, capable of allowing gas to move to waste receptacle and preventing movement of media 8020 into it while simultaneously maintaining sterility of the device and its fluid connections. Skilled artisans are encouraged to recognize that pressure balance conduit 8033B need not be attached to media removal conduit 8010, but can instead be a separate conduit interfaces with a peristaltic pump. In this case, preferably a multichannel peristaltic pump is used that is connected to the media removal conduit and the pressure balance conduit. In such configurations, peristaltic pump 8030 draws gas from below growth surface 8006, pulling a vacuum on growth surface 8006 that counter balances the vacuum being created within cell growth and cell recovery device 8000, thereby holding growth surface 8006 in a substantially horizontal state, or at a minimum lessening in the distortion experienced by growth surface 8006. Skilled artisans are encouraged to recognize that any apparatus that draws gas out of the pressure balance conduit can achieve the purpose of preventing potentially damaging distortion to the growth surface as media is removed.

Growth surface support 8018 is designed to interface with liquid removal adaptor 8027 and growth surface support 8018 is designed to interface with cell culture and cell culture recovery device 8000 in a manner that allows gas to be removed from gas space 8019 at a rate that allows the pressure adjacent and external to the growth surface to be equal or less than the pressure of internal volume 8014. Skilled artisans are advised to recognize that the interfaces need not be an air tight seal so long as it exerts control over gas space 8019 pressure. Preferably however, seals are provided. Skilled artisans should also be advices that liquid removal adapter 8027 need not be required to achieve the objective of maintaining the growth surface in a substantially horizontal state as media is drawn from the cell culture and cell recovery device. For example, pressure balance conduit 8033B can interface directly with gas access opening(s) 8021. In any event, if used, the liquid removal adaptor is preferably easily connected and disconnected from the growth surface support such that when disconnected, ambient gas can make passive contact with the growth surface without need of any mechanisms or processes to force gas. Skilled artisans should be aware that the growth surface support need not be permanently attached to the cell culture and cell recovery device.

Figure 11:
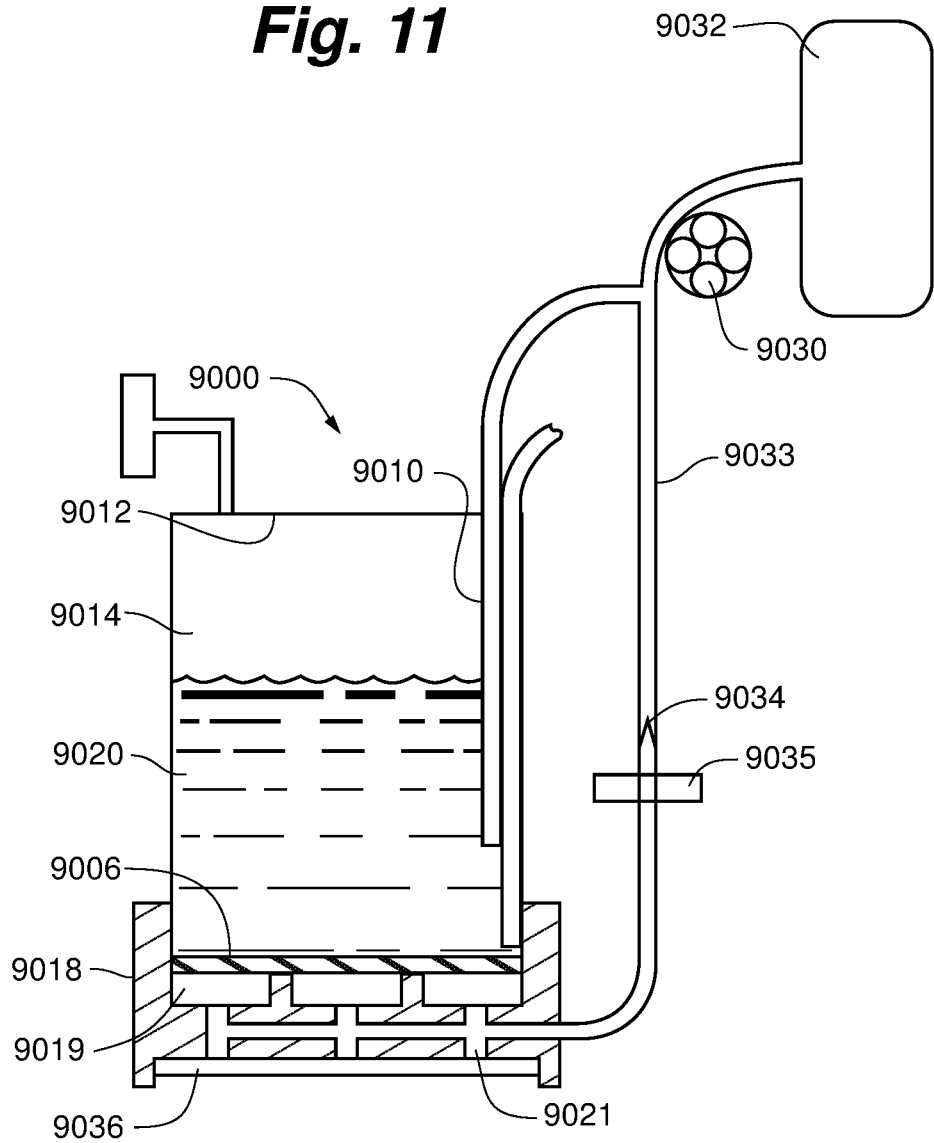
FIG. 11 shows a cross-sectional view of a gas permeable cell culture device and a process by which the growth surface remains in a planar position during media and cell removal.

FIG. 11 shows another embodiment of a cell culture and cell recovery device adapted to allow media to be withdrawn from the device with substantially little distortion of the growth surface. Cell growth and cell recovery device 9000 includes growth surface support 9018. Growth surface support 9018 includes gas access opening(s) 9021. Gas access opening(s) 9021 allow passive movement of ambient gas to and from growth surface 9006, which is preferably gas permeable, liquid impermeable, and residing in a horizontal plane during cell culture. Gas access opening filter 9036 prevents contaminants from accessing gas access opening(s) 9021. Skilled artisans are advised that the material selected for the gas access opening filter can be any such that it acts as a sterile barrier and allows passive gas access to the growth surface at a rate that allows adequate oxygenation of the culture. Preferably, it is a porous material with pore sizes of less than 0.45 microns and more preferably less than 0.22 microns. Media removal conduit 9010 is attached to waste receptacle 9032 and interfaces with and peristaltic pump 9030 in a manner such that peristaltic pump 9030 is able to draw media 9020 out of cell growth and cell recovery device 9000. Pressure balance conduit 9033 links media removal conduit 9010 to gas space 9019 and may optionally contain check valve 9034 (to prevent media from potentially entering the gas space) and/or pressure balance conduit filter 9036 (to prevent contaminants or biohazards from potentially entering the gas space and then potentially crossing the gas access opening filter). During media removal, the peristaltic pump rate is such that a pressure in gas space 9019 (i.e. the space between growth surface 9006 and gas access opening filter 9036) is less than or equal to the pressure of internal volume 9014, thereby minimizing and/or preventing movement of growth surface 9006 towards upper confine 9012. Preferably, the pressure balance conduit is a flexible tube that mates to a tube emanating from an accessing opening to the gas space, and a sterile tubing weld is used to create the mate.

Figure 12A:
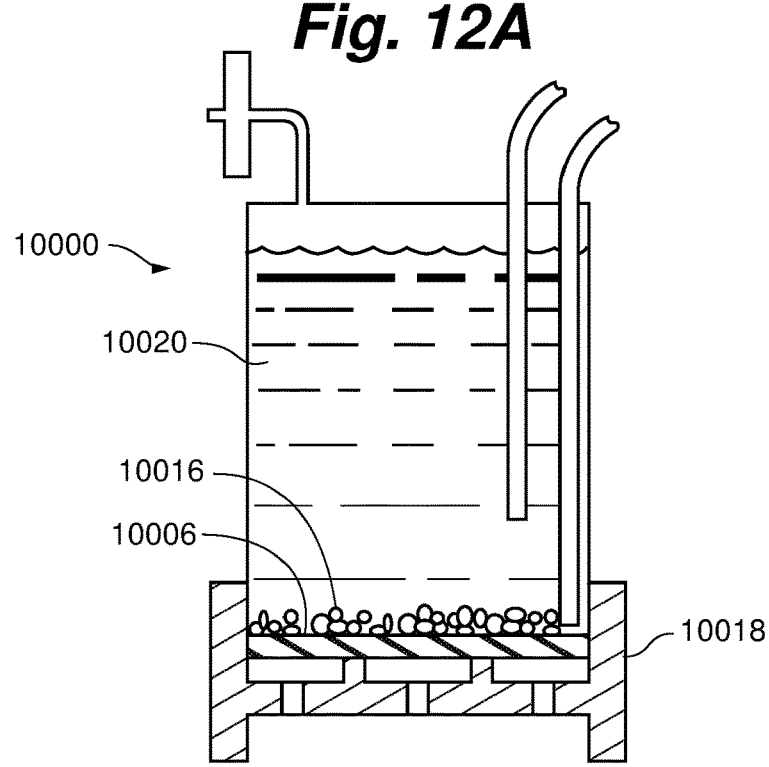
FIG. 12A and FIG. 12B show a cross-sectional view of a gas permeable cell culture device and a process by which the growth surface remains in a planar position during media and cell removal.
Figure 12B:
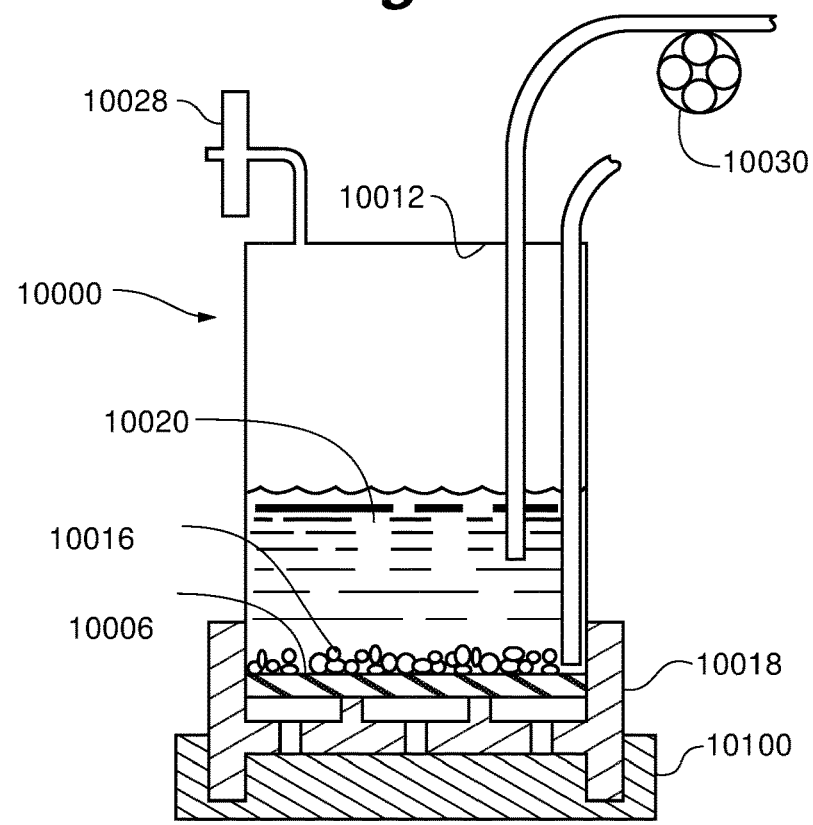

Yet another embodiment for a cell culture and cell recovery device and process is shown in FIGS. 12A and 12B. In this embodiment, the internal volume of the cell culture and cell recovery device is placed at a pressure that is less than that of the ambient environment as media is pulled out of the cell culture and cell recovery device. FIG. 12A shows cell culture and cell recovery device 10000 shown in a state of static cell culture. Cells 10016 have gravitationally settled onto gas permeable, liquid impermeable, growth surface 10006. In FIG. 12B, ambient gas restrictor 10018 is in contact with cell culture and cell recovery device 10000. Ambient gas restrictor 10018 acts to limit ambient gas contact with growth surface 10006 in order to limit the pressure imbalance across growth surface 10006 when liquid is pulled from cell culture and cell recovery device 10000. In this example, peristaltic pump 10030 acts to draw media 10020 out of media removal conduit 10010. As media is drawn out of the cell culture and cell recovery device, a pressure drop becomes present when gas is restricted from entering the device by vent filter 10028. Despite the pressure of the internal volume of cell culture and cell recovery device 10000 having been reduced relative to the ambient environment, growth surface 10006 is prevented from experiencing the relative pressure imbalance by ambient gas restrictor 10100. Ambient gas restrictor 10100 need not make a gas tight connection to cell culture and cell recovery device 10000, but that is preferable if one wishes to limit substantial movement of the growth surface toward upper confine 10012. The process of reducing media volume prior to cell recovery can be carried out as previously described using one or more conduits. Preferable, if present, growth surface support 10018 is designed to minimize gas within it.

Yet another embodiment for a cell culture and cell recovery device and process is shown in FIGS. 13A, 13B, and 13C. In this approach, a fixed and predetermined volume of gas is injected into the cell culture and cell recovery device. Although the source of the injected gas in this illustrative embodiment is a position, skilled artisans are encouraged to recognize that the source can be any mechanism(s) able to dispense a known volume of gas, such as a bellows. As shown in FIG. 13A, cell culture and cell recovery device 11000 is shown in a state of static cell culture and includes initial media volume 11020A and cells 11016. Piston 11100 is connected to cell culture and cell recovery device 11000 by way of vent filter 11028. As shown in FIG. 3B, when waste media is to be removed, piston head 11150 moves a first predetermined distance to drive a volume of gas into cell culture and cell recovery device 11000. The volume of gas drives an equal volume of media out of media removal conduit 11010, which is open to a waste receptacle (not shown for clarity). Upon completion of this step, media removal conduit 11010 is closed to the waste receptacle and a residual media volume 11020B remains in cell culture and cell recovery device 11000 along with cells 11016. As shown in FIG. 13C, when cells 11016 and residual media 11020B are to be removed, piston 11100 moves a second predetermined distance to dispense an additional volume of gas into cell culture and cell recovery device 11000, thereby driving cells 11016 and the residual media volume 11020B through an open cell removal conduit 11004 and into a cell collection receptacle (not shown for clarity).

Those skilled in the art will recognize that numerous modifications can be made thereof without departing from the spirit. Therefore, it is not intended to limit the breadth of the invention to the embodiments illustrated and described. Rather, the scope of the invention is to be interpreted by the appended claims and their equivalents. Each publication, patent, patent application, and reference cited herein is hereby incorporated herein by reference.

The invention claimed is:

1. A method of removing media and cells from a cell culture device, the method comprising:
   using the cell culture device which comprises a growth surface to reduce a volume of a liquid media in the cell culture device, said device comprising
   a gas delivery component,
   a first fluid detection component that is capable of determining when the liquid media moving within a media removal conduit, which is connected to the cell culture device that comprises a media removal opening, is replaced by a gas, said first fluid detection component capable of sending a signal to a first fluid flow control component that is capable of terminating the liquid media flow through the media removal conduit,
   a second fluid detection component that is capable of determining when the liquid media moving within a cell removal conduit that is connected to the cell culture device to is replaced by a gas, said second fluid detection component capable of sending a signal to a second fluid flow control component that is capable of terminating the liquid media flow through the cell removal conduit; said cell culture device comprising a gas permeable bottom upon which cells reside, and a filter;
   increasing the concentration of cells per milliliter of liquid media within said cell culture device by connecting said gas delivery component to said filter,
   connecting said first fluid detection component to the outside of said media removal conduit, connecting said first fluid flow control component to said media removal conduit,
   initiating gas delivery from said gas delivery component, whereby gas moves into said cell culture device and displaces liquid media and cells from said cell culture device into a cell collection vessel connected to said cell removal conduit, said second fluid detection component determines when liquid media that is moving through said cell removal conduit is replaced by a gas and sends a signal to said second fluid flow control component which then terminates the flow of liquid media through said cell removal conduit,
   removing cells from said gas permeable cell culture device by connecting said second fluid detection component to the outside of said cell removal conduit,
   connecting said second fluid flow control component to said cell removal conduit, and
   initiating gas delivery from said gas delivery component, whereby gas moves into said cell culture device and displaces liquid media and cells from said cell culture device into a cell collection vessel connected to said cell removal conduit, said second fluid detection component determines when the liquid media that is moving through said cell removal conduit is replaced by a gas and sends a signal to said second fluid flow control component which then terminates the flow of liquid media through said cell removal conduit.

2. The method of claim 1 wherein after said second flow control component has terminated the flow of fluid through said cell removal conduit, the method further comprising;
   venting said cell culture device to atmosphere, said first flow control component is opened to allow the flow of liquid media through said media removal conduit, liquid media is moved through said media removal conduit into said cell culture device, said first flow control component is closed, and said cell culture device is no longer vented to atmosphere, and
   delivering gas from said gas delivery component into said cell culture device to displace liquid media and cells from said cell culture device into a cell collection vessel connected to said cell removal conduit, said second fluid detection component determining when the liquid media that is moving through said cell removal conduit has been replaced by a gas and upon making that determination said second fluid detection component sends a signal to said second fluid flow control component and upon receiving said signal, said second flow control component terminates the flow of liquid media through said cell removal conduit.

3. The method of claim 1 wherein the gas permeable material is in contact with a gas permeable material support.

4. The method of claim 1 wherein the gas permeable material of the cell culture device is comprised of silicone.

5. The method of claim 4 wherein the gas permeable material has a thickness between 0.001 inches and 0.024 inches.

6. The method of claim 1 wherein the growth surface of said cell culture device is in a substantially horizontal state when gas displaces liquid media from the cell culture device.

7. The method of claim 1 wherein prior to reducing the volume of liquid media the lowest point of the liquid media to the highest point of the liquid media is from 1.0 cm to 10.0 cm.

8. The method of claim 1 wherein said cells are comprised of T cells.

9. The method of claim 1 wherein said cells are comprised of chimeric antigen receptor (CAR) T cells.

10. The method of claim 1 wherein prior to the removing cells, the method further comprises adding fresh liquid media to said cell culture device through said media removal conduit.

11. The method of claim 1 wherein said gas delivery component is a diaphragm pump.

12. The method of claim 1 wherein the media removal conduit within the cell culture device shares a wall with the cell culture device.

13. The method of claim 1 wherein the distance between the media removal opening and the growth surface is reduced after the first flow control component terminates the flow of liquid media through said media removal conduit.

14. The method of claim 13 wherein the cell culture device includes a cell collection pocket in the growth surface which the media removal conduit resides during the step of collecting cells.

15. The method of claim 1 wherein prior to the removal of cells, agitating the device to dislodge cells from the growth surface.

16. The method of claim 1 wherein during the step of collecting cells the device is oriented into a position that places the cell removal conduit at the low point of the device.

17. The method of claim 1 wherein a portion of the cell removal conduit is positioned within a pocket within the gas permeable bottom of said cell culture device.

18. The method of claim 1 wherein when second fluid flow control component terminates the flow of liquid media through said cell removal conduit, said gas delivery component terminates gas delivery.

19. The method of claim 1 wherein said gas delivery component includes a pressure relief valve.

* * * * *